United States Patent [19]
Stroebel

[11] Patent Number: 5,861,012
[45] Date of Patent: *Jan. 19, 1999

[54] ATRIAL AND VENTRICULAR CAPTURE DETECTION AND THRESHOLD-SEEKING PACEMAKER

[75] Inventor: John C. Stroebel, Blaine, Minn.

[73] Assignee: Medtronic, Inc., Minneapolis, Minn.

[ * ] Notice: The term of this patent shall not extend beyond the expiration date of Pat. No. 5,601,615.

[21] Appl. No.: 732,755

[22] Filed: Oct. 18, 1996

Related U.S. Application Data

[60] Division of Ser. No. 291,304, Aug. 16, 1994, Pat. No. 5,601,615, and a continuation-in-part of Ser. No. 291,304.

[51] Int. Cl.$^6$ ........................................... A61N 1/37
[52] U.S. Cl. .................................................... 607/28
[58] Field of Search ...................... 607/28, 11, 25, 607/27

[56] References Cited

U.S. PATENT DOCUMENTS

| | | |
|---|---|---|
| 4,257,423 | 3/1981 | McDonald et al. . |
| 4,374,382 | 2/1983 | Markowitz ................. 340/870.01 |
| 4,428,378 | 1/1984 | Anderson et al. . |
| 4,556,063 | 12/1985 | Thompson . |
| 4,729,376 | 3/1988 | DeCote . |
| 5,052,388 | 10/1991 | Sivula et al. . |
| 5,127,404 | 7/1992 | Wyborny et al. . |
| 5,165,404 | 11/1992 | Anderson et al. . |
| 5,165,405 | 11/1992 | Ekwall . |
| 5,172,690 | 12/1992 | Nappholz . |
| 5,222,493 | 6/1993 | Sholder . |
| 5,285,780 | 2/1994 | Tsuji et al. ................. 607/13 |
| 5,320,643 | 6/1994 | Roline et al. ............... 607/28 |
| 5,324,310 | 6/1994 | Greeninger et al. ........ 607/28 |
| 5,476,486 | 12/1995 | Lu et al. ..................... 607/28 |
| 5,507,782 | 4/1996 | Kieval et al. ............... 607/9 |

FOREIGN PATENT DOCUMENTS

WO94/12237  6/1994  WIPO ............. A61N 1/365

OTHER PUBLICATIONS

Strauss Harold C. et al Electrophysiologic Evaluation of Sinus Node Function in Patients with Sinus Node Dysfunction. vol. 53, No. 5, May 1976.

Strauss Harold C. et al Premature Atrial Stimulation as a Key to the Understanding of Sinoatrial Conduction in Man. vol. XLViI Jan. 1973.

*Primary Examiner*—Scott M. Getzow
*Attorney, Agent, or Firm*—Harold R. Patton; Michael B. Atlass

[57] ABSTRACT

Capture detection and stimulation threshold-measurement methods and apparatus for deriving atrial and ventricular pace pulse (A-pace and V-pace) stimulation energy strength-duration data. In a first atrial and ventricular threshold test regimen for use with patients having intact A-V conduction or first degree AV block, A-pace pulses are delivered at a test escape interval and A-V delay. Atrial loss of capture (ALOC) in response to an A-pace test stimulus is declared by the absence of a detected ventricular depolarization (V-event) in the latter portion of the paced A-V delay interval following the delivery of the A-pace test stimulus. In the ventricular threshold test regimen, a V-pace test stimulus is delivered after a shortened A-V delay. Ventricular loss of capture (VLOC) is declared by the detection of a V-event in the ventricular refractory period of the V-pace test stimulus. In a second algorithm for use in the atrium or ventricle in patients having regular measured sinus rhythm, premature A-pace or V-pace test stimuli are delivered, and the presence of an A-event or V-event at the end of the measured sinus escape interval is declared to be ALOC or VLOC, respectively. A-pace and V-pace test stimuli are repeated to confirm capture declarations at an energy exceeding the LOC test energy. The atrial and ventricular stimulation threshold data derived by varying both pulse amplitude (strength) and width (duration) is stored in memory for telemetry out and analysis and for use in setting the V-pace and A-pace normal pulse width and amplitude used between successive auto-capture tests in order to conserve battery energy.

10 Claims, 19 Drawing Sheets

ATRIAL AND VENTRICULAR CAPTURE DETECTION AND THRESHOLD-SEEKING PACEMAKER

This is a divisional and a continuation in part of application Ser. No. 08/291,304 now issued as U.S. Pat. No. 5,601,615, and filed on Aug. 16, 1994.

FIELD OF THE INVENTION

The present invention generally relates to implantable pacemakers and more particularly to a method and apparatus for testing and detecting capture of the heart in both chambers of the heart, deriving and storing stimulation signal threshold data, and adjusting stimulation signal energy for energy efficiency.

BACKGROUND OF THE INVENTION

As described in commonly assigned U.S. Pat. No. 5,320,643, incorporated herein by reference, a cardiac pacemaker is an electrical device used to supplant some or all of an abnormal heart's natural pacing function by delivering appropriately timed electrical stimulation signals designed to cause the myocardium of the heart to contract or "beat", i.e. to "capture" the heart. Stimulation pulses provided by implanted pacemakers usually have well-defined amplitude and pulse width characteristics which can be adjusted by remote programming and telemetry equipment to meet physiologic and device power conservation needs of the particular patient.

The strength (amplitude) and duration (pulse width) of the pacing pulses must be of such an energy magnitude above the stimulation threshold that capture is maintained to prevent serious complications and even death. Yet, it is desirable for these energy magnitudes not to be higher than the stimulation threshold than is needed for a reasonable "safety margin" in order to prolong battery life. The patient's stimulation thresholds in the atrium and ventricle often fluctuate in the short term, and gradually change in the long term. It has been clinically observed that the lowest stimulation threshold is observed immediately after implantation of the pacemaker (the acute threshold). Inflammation in the cardiac tissue around the tip of the pacing lead electrode drives the stimulation threshold up sharply during the first two to six weeks after implant to its highest level (the peak threshold), and greater pacing pulse energy is required to effect capture. Some of the inflammation reduces over the long-term, to lower the threshold below the peak level—the chronic threshold. However, the chronic threshold does not reduce to the acute level, since some permanent fibrous tissue, requiring greater energy than non-fibrous tissue for signal propagation, remains around the electrode tip. In the short-term, thresholds may decrease with exercise, for example, and may increase with various activities, including sleep. Consequently, the safety margin is typically set by the physician on implantation of the pacemaker to account for projected maximal stimulation thresholds.

As described in commonly assigned U.S. Pat. No. 5,324,310, incorporated herein by reference, the post-operative determination of the stimulation thresholds by the physician typically requires the patient to be connected to surface ECG equipment while a threshold routine is conducted using the pacemaker programmer. The pacemaker programmer remotely effects the successive temporary reprogramming of the pulse width and/or amplitude to ascertain the points at which capture is lost, and a strength-duration curve may be plotted from the resulting threshold data. In this process, pacing pulses are delivered to either heart chamber at a test pacing rate above the patient's own underlying rate, and the pace pulse energy is decreased from pulse to pulse in a preset pattern. The pacing pulses are observed on a display or paper tracing as spikes, and capture or loss of capture is observed by the presence or absence of the evoked cardiac response waveshape (a P-wave or an R-wave) that follows each spike. At loss of capture, the pacing pulse energy may be immediately restored so that the patient does not experience syncope. The resulting threshold data may be used to permanently reprogram the pulse energy. Naturally, such periodic patient studies are time consuming and expensive to conduct. Moreover, they do not provide an indication of stimulation threshold fluctuation over the course of a patient's day and levels of activity. The life of the implantable pulse generator (IPG) is shortened as the battery is depleted at a rate higher than necessary to meet the patient's needs.

As a result of these considerations, a great deal of effort has been expended over many years to develop IPGs having the capability of automatically testing the stimulation threshold, i.e. providing an "auto-capture" detection function, and resetting the pacing pulse energy to exceed the threshold by the safety margin without the need for clinical or patient intervention. A wide variety of approaches have been taken as reflected by the extensive listing of earlier patents described in the commonly assigned '310 and '643 patents and in further U.S. Pat. Nos. 5,165,404, 5,165,405, 5,172,690, 5,222,493 and 5,285,780.

In such IPGs, the capture detection approaches have taken a variety of forms typically in the attempt to overcome the difficulty in detecting the evoked cardiac response wave shape from the pacing electrodes employed to deliver the pacing pulse. The high stimulation energy pacing pulse and the ensuing after-potentials and electrode-tissue polarization artifacts mask the evoked response, and also saturate the sense amplifiers coupled to the electrodes, until they dissipate. By the time that the sense amplifier is no longer blinded, the evoked response, if any, has typically passed the electrodes. Many of the approaches that have been taken include blanking intervals for the sense amplifiers combined with efforts to suppress or attenuate or compensate electronically for the composite post-delivery signal levels at the sense amplifier input during the blanking intervals to shorten the saturation period (and the blanking interval) as much as possible.

Alternatively, the use of separate "far field" EGM amplifiers and electrode systems from those "near field" electrode systems used in delivering the pacing pulse have been proposed in a variety of configurations, as exemplified by the above referenced '310 patent.

In a further approach, one or more physiologic sensors that show a response to the mechanical action of the heart, e.g. a piezoelectric or impedance sensor, or that show changes in physical properties of the blood when the heart is captured, e.g. blood pH, temperature, impedance or blood pressure sensors on the pacing lead have also been suggested as exemplified by the above referenced '643 patent.

The function and accuracy of the these approaches have been adversely affected by one or more of factors including, but not limited to: myopotentials (electrical signals which are the product of muscle movement) in the case of EGMs; stray electromagnetic interference (EMI); problems with the sensor sensitivity (either too sensitive or not sensitive enough); and, in the case of pressure sensors, variations of the sensed electrical signals as a result of changes in thoracic pressure (for example, due to respiration, coughing or sneezing).

In virtually all of the approaches, it is necessary to rely on additional components and circuitry which consume more energy and add to the bulk and cost of the system and raise reliability issues. The additional components and circuitry are increased further in dual chamber pacemakers, where the difficulty of detecting the evoked P-wave is further complicated by its relatively low amplitude. Very few of the numerous approaches of the prior art have been attempted in an implantable pacemaker system and fewer yet have been proven clinically useful and commercially successful.

SUMMARY OF THE INVENTION

In view of the foregoing, it is a first object of the present invention to provide a cardiac pacemaker having a capture detection feature in which atrial and ventricular capture may be detected and distinguished without the use of any additional components, e.g. special leads, electrodes or sensors or additional circuitry to that normally present in a microprocessor based dual chamber IPG.

It is a further object of the invention, in a dual chamber pacemaker, to measure atrial stimulation thresholds by applying a test stimulus in the atrium and detecting loss of capture of the atrium in the ventricle from the absence of a conducted ventricular depolarization occurring within a certain atrial-ventricular time interval following delivery of the atrial stimulus.

It is a still further object of the invention, in a dual chamber pacemaker, to measure ventricular stimulation thresholds by applying a test stimulus in the ventricle following delivery of an atrial pace pulse and detecting loss of capture from the presence of a conducted ventricular depolarization in an atrial-ventricular time window following delivery of the ventricular stimulus.

It is yet another object of the invention to measure either atrial or ventricular stimulation thresholds in the atrium or the ventricle, respectively, by applying a test stimulus prematurely timed with respect to a previous atrial or ventricular beat and detecting loss of capture from the presence of an atrial or ventricular beat following the earlier beat at the end of the expected sinus escape interval.

It is yet a further object of the present invention to provide a regimen for periodic atrial and ventricular threshold testing and derivation of atrial and ventricular strength-duration data, adjusting the atrial and ventricular pacing pulse amplitude and width in relation to the atrial and ventricular threshold data, storing the data and reading out the data and current pacing pulse amplitudes and widths on command of an external programmer.

These and other objects of the invention are realized in automatic capture detection and stimulation threshold-seeking methods and apparatus for use with a dual chamber or a single chamber cardiac pacemaker IPG operating to perform the above stated objects to derive atrial and/or ventricular pace pulse (A-pace and V-pace) stimulation energy strength-duration data.

In a first aspect of the invention particularly for use with patients having intact and regular A-V conduction or first degree block, an atrial and ventricular threshold test regimen, A-pace pulses are delivered at a test escape interval and A-V delay. Atrial loss of capture (ALOC) in response to a triggered A-pace test stimulus is declared by the absence of a detected ventricular depolarization (V-event) in the latter portion of the paced A-V delay interval following the delivery of the A-pace test stimulus. In the ventricular threshold test regimen, a V-pace test stimulus is delivered after a shortened A-V delay from the preceding A-pace. Ventricular loss of capture (VLOC) is declared by the detection of a V-event in the ventricular refractory period of the V-pace test stimulus.

In a second aspect of the invention, for use in the atrium or ventricle in patients having regular measured sinus rhythm, premature A-pace or V-pace test stimuli are delivered at a test escape interval set as a fraction of the average measured escape interval. The presence of a following A-event or V-event, respectively, outside a not reset window set to be somewhat longer than the test escape interval is declared to be ALOC or VLOC, respectively. Preferably, in this embodiment, the test stimuli energy in pulse width and amplitude is increased until CAPTURE is declared so that the patient's normal rythm is not disturbed frequently during the test.

A-pace and V-pace test stimuli are repeated to confirm capture declarations at an energy exceeding the LOC test energy. The atrial and ventricular stimulation threshold data derived by varying both pulse amplitude (strength) and width (duration) at both LOC and capture test values is stored in memory for telemetry out and analysis and also for use in setting the V-pace and A-pace normal pulse width and amplitude used between successive threshold measurement tests The resulting A-pace and V-pace stimulation threshold pulse amplitudes and pulse widths may be stored in existing memory for retrieval using existing telemetry and external programmers. In the IPG, the normal A-pace and/or V-pace pulse widths and amplitudes may be changed, if appropriate, from the programmed or previously set values taking the appropriate safety margin into account in order to conserve battery energy.

Advantageously, the methods and apparatus of the present invention may be applied to a programmable single chamber IPG or a multi-programmable DDD(R) IPG by simply storing the operating algorithm in memory to periodically perform the threshold measurement method. No additional circuitry, sensors or other components are necessary to practice the methods. The pacemaker pulse generator is effectively reconfigured to establish threshold test A-pace and/or V-pace escape intervals, A-V delay intervals, and other timing intervals, to operate the atrial and/or ventricular pulse generators to deliver the A-pace and/or V-pace test stimuli at varying pulse widths and amplitudes, to process the V-event signals of the ventricular sense amplifier and to declare ALOC and VLOC at the stimulation threshold for A-pace and V-pace pulse width and amplitude.

BRIEF DESCRIPTION OF THE DRAWINGS

These and other advantages, objects and features of the invention will be further understood when reference is made to the following description, taken in conjunction with the accompanying drawings, in which.

DETAILED DESCRIPTION OF THE PREFERRED EMBODIMENT

In accordance with a first aspect of the invention, the inventive apparatus and methods are incorporated into a dual chamber IPG as described in the following FIGS. 1–9 particularly for use with patient's having intact and regular AV conduction or first degree AV block. In a further aspect of the invention, an algorithm is set forth in FIG. 10 for making threshold measurements in a single chamber pacemaker or in a single chamber of a dual chamber pacemaker, particularly for patients only needing single chamber pacing or lacking intact, regular AV conduction. The following detailed description of a multi-programmable, rate responsive, dual chamber IPG and remote programmer provides a preferred mode in which either or both aspects of the invention may be incorporated. It will be understood that the single chamber pacemaker or pacing modes would selectively incorporate features of the particularly described IPG and programmer architecture as necessary.

PART I. DESCRIPTION OF THE IPG AND LEADS.

Figure 1:
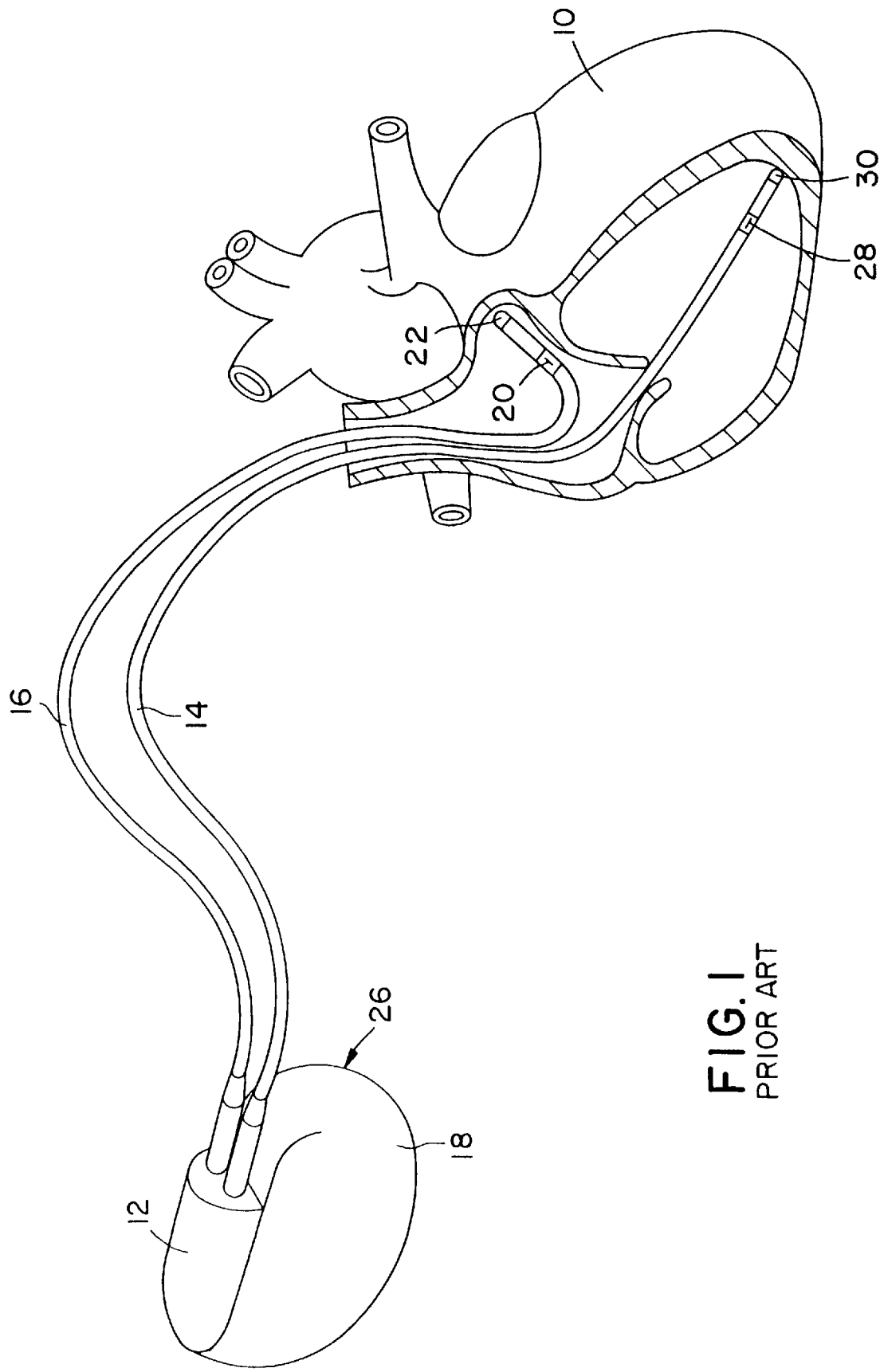
FIG. 1 is an illustration of a dual chamber pacemaker according to the present invention in conjunction with an associated set of cardiac pacing leads, illustrated as located in a cutaway view of a human heart.
Figure 2:
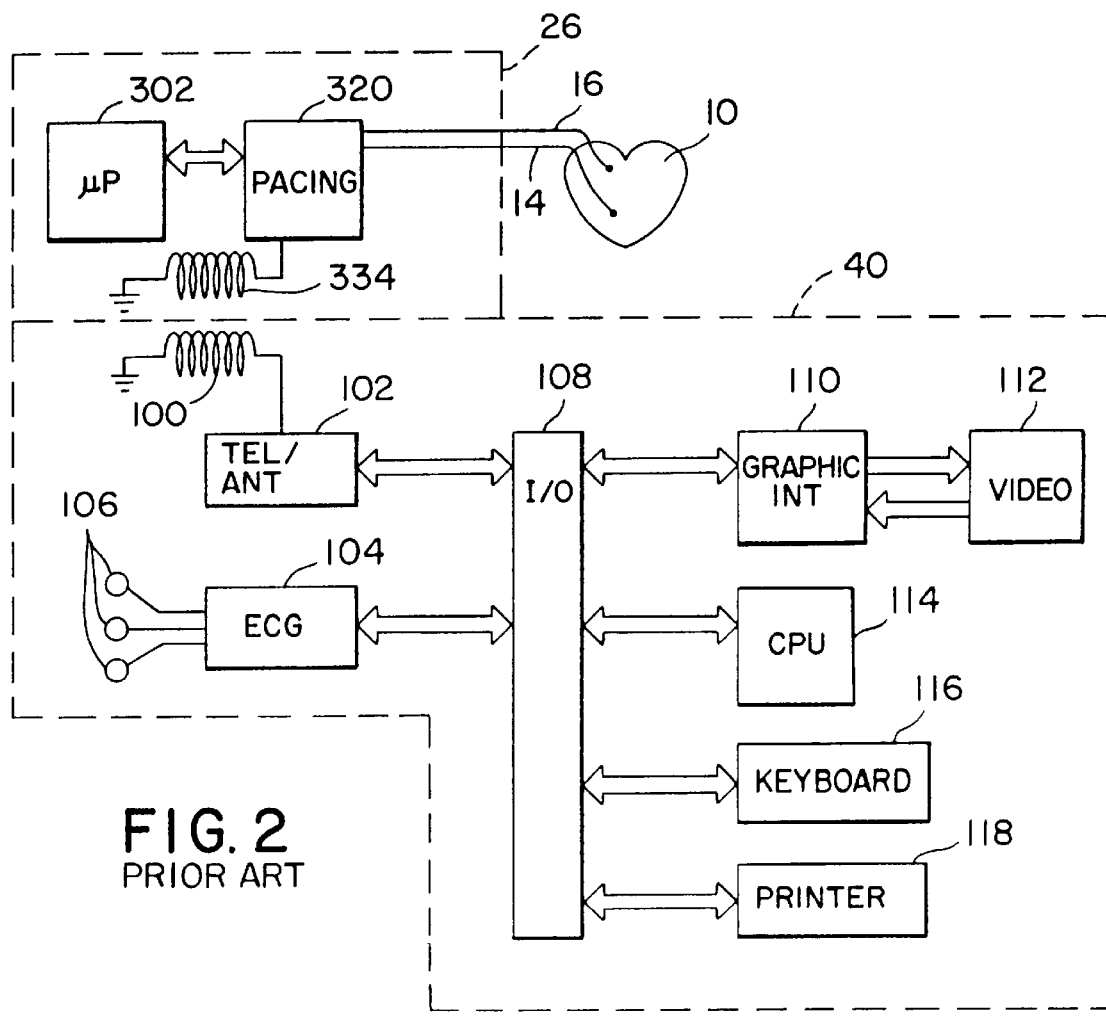
FIG. 2 is a functional block diagram of the dual chamber pacemaker illustrated in FIG. 1 in conjunction with an external programmer/monitoring unit, for use in performing the atrial and ventricular capture detection and auto threshold setting functions of the present invention.
Figure 3:
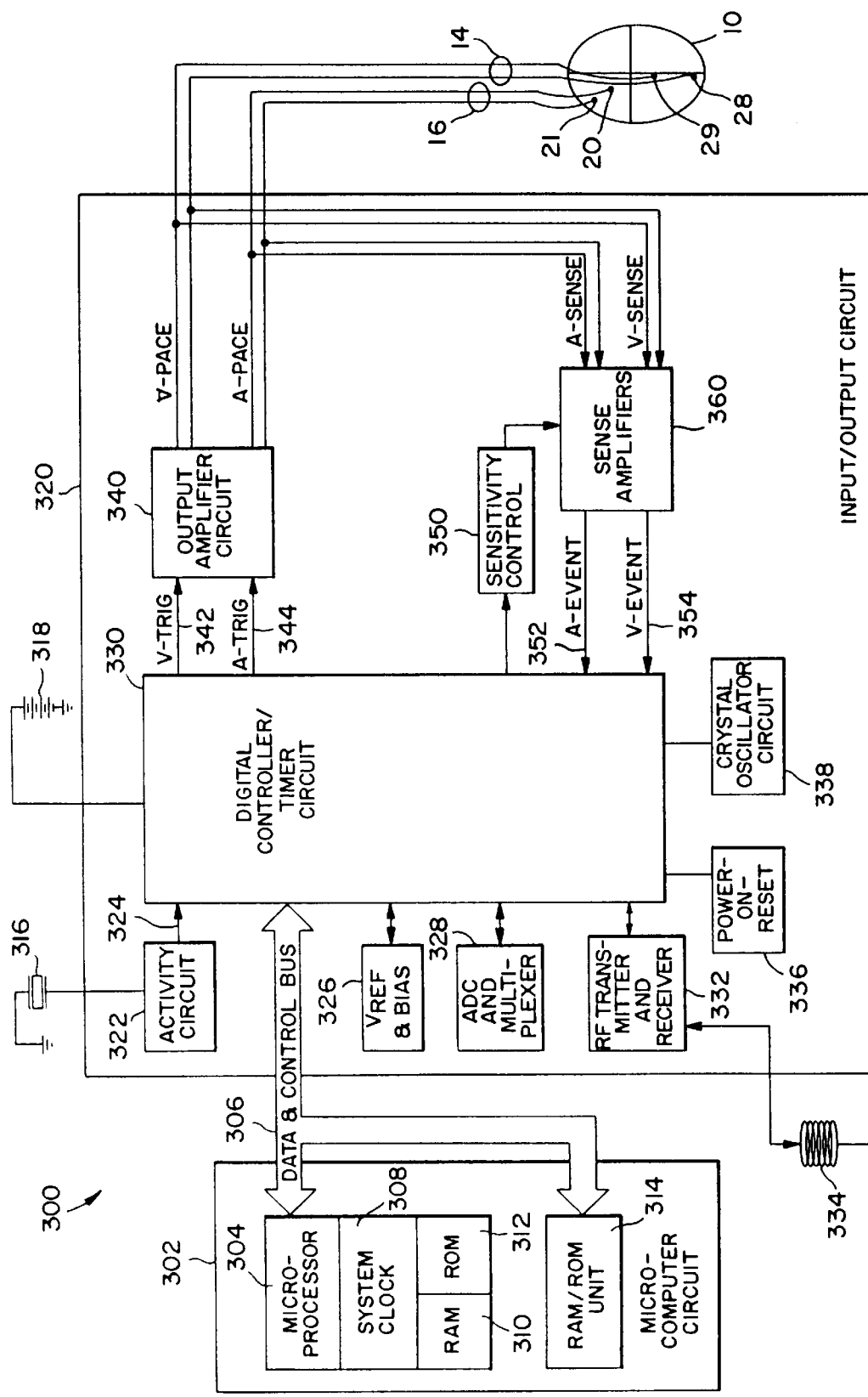
FIG. 3 is a block diagram of the dual chamber pacemaker illustrated in FIGS. 1 and 2, illustrating the functional components of the device in more detail.
Figure 4:
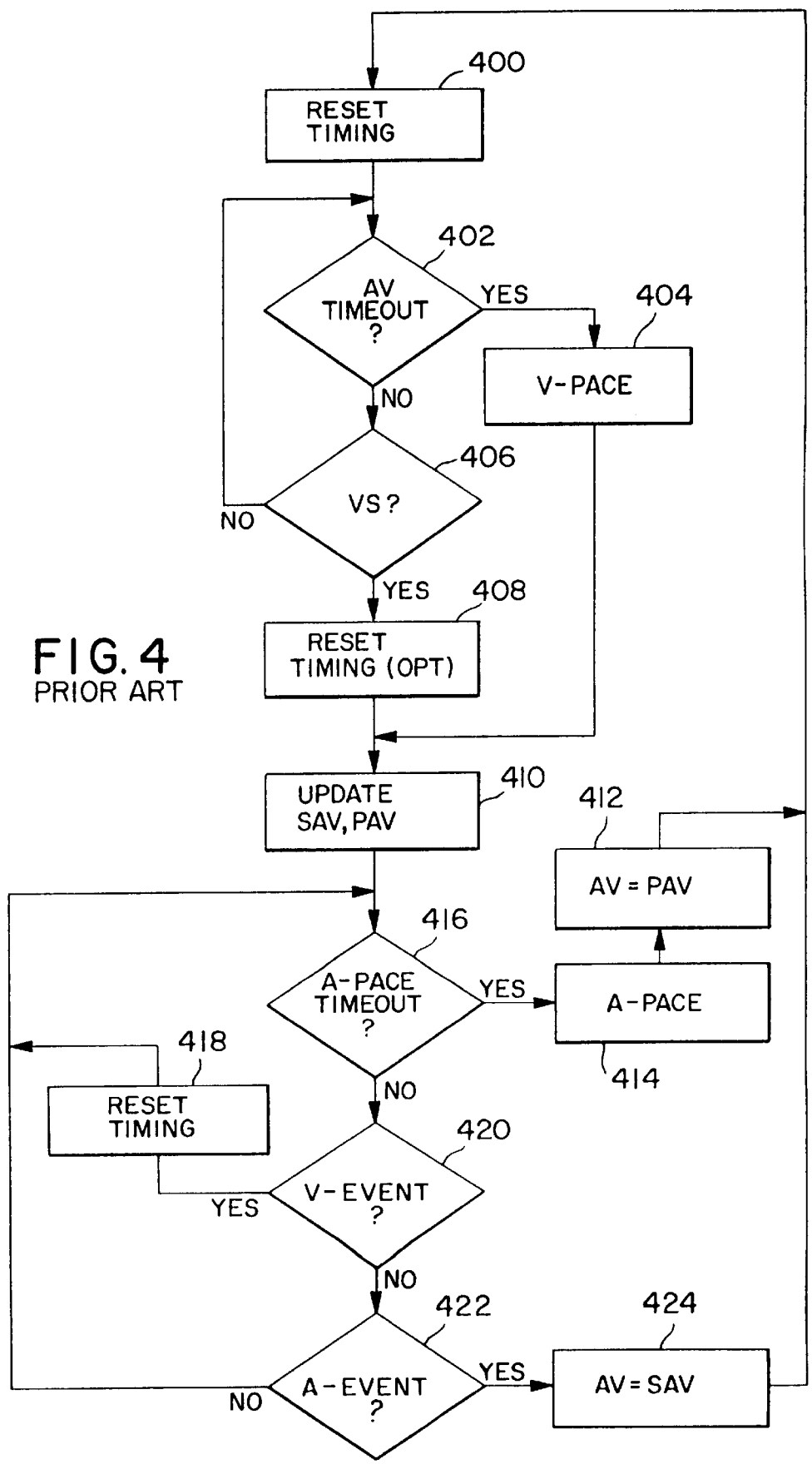
FIG. 4 is a flow chart of the overall operation of the pacemaker of FIGS. 1–3.

FIG. 1 illustrates the external configuration of a dual chamber IPG 26, which is provided with a hermetically sealed enclosure 18, typically fabricated of biocompatible metal such as titanium. Mounted to the top of the enclosure 18 is a connector block assembly 12, which receives electrical connectors located on the proximal ends of leads 14 and 16. The combination of the leads 14 and 16 and the IPG 26 constitute an implantable pacemaker. FIGS. 1–3 and related FIG. 4 are described in U.S. patent application Ser. No. 08/214,933, filed Mar. 17, 1994, entitled METHOD AND APPARATUS FOR DUAL CHAMBER CARDIAC PACING which application is hereby incorporated by reference.

Lead 16 is an atrial bipolar pacing lead, carrying two electrodes 20 and 22. Electrodes 20 and 22 are used both to sense atrial depolarizations (P-waves) and to deliver atrial pacing pulses. Atrial pacing pulses may be delivered between electrodes 20 and 22 in a bipolar pacing mode or between electrode 22 and the housing 18 of the IPG 26 in a unipolar pacing mode. Sensing of P-waves may occur between electrode 20 and electrode 22 in a bipolar sensing mode or between either of electrode 20 and 22 and the housing 18 of the IPG 26 in a unipolar sensing mode.

Similarly, lead 14 represents a ventricular bipolar pacing lead, carrying two electrodes 28 and 30. As discussed above in conjunction with atrial lead 16, electrodes 28 and 30 are used to sense and pace the ventricle. Bipolar ventricular pacing may be accomplished between electrodes 30 and 28 or unipolar ventricular pacing may be accomplished between electrode 30 and the conductive housing 18 of IPG 26. Sensing of ventricular depolarizations or R-waves may be accomplished between electrodes 30 and 28 in a bipolar sensing mode or between either of electrodes 30 and 28 and the housing 18 of the IPG 26 in a unipolar sensing mode.

As discussed below, the specific embodiment of the IPG 26 disclosed preferably operates in a DDD or DDDR pacing mode, wherein pacing pulses are delivered to both atrium and ventricle and wherein sensed atrial and ventricular depolarizations are both effective to inhibit delivery of the next scheduled pacing pulse in the chamber in which they are detected. The atrial and ventricular capture detection from the ventricular electrodes afforded by the present invention is believed optimally practiced in a pacemaker operating in the DDD, DDI, DVI, DDDR, DVIR and DDIR pacing modes.

FIG. 2 illustrates the IPG 26 in block diagram form, coupled to a human heart 10 through the leads 14, 16, in conjunction with an external programmer 40 corresponding to those typically employed to program modern, multi-programmable implantable pacemakers. Within the housing of the IPG 26 are located the pacing circuitry 320, which includes circuitry performing all of the basic timing, stimulation and sensing functions of a DDD or DDDR cardiac pacemaker, and a microcomputer circuit 302, which controls the timing intervals provided by the pacing circuitry 320. Pacing circuitry 320 also includes a bi-directional telemetry circuit coupled to an antenna 334, allowing transmission of information from external programmer 40 into the IPG 26 to modify its parameters and allowing transmission of information from the IPG 26 to the external programmer 40, again generally corresponding to telemetry and programming systems presently existing in commercially marketed multi-programmable implantable pacemakers.

The programmer 40 also includes a telemetry antenna 100 coupled to a telemetry/antenna driver circuit 102 which serves to demodulate telemetry signals received from antenna 334 of the IPG 26, and to apply them in parallel or serial digital format to input/output (I/O) unit 108. The telemetry signals in turn may be applied to a video monitor 112, via graphic interface 110, and/or provided to central processing unit 114 and/or printer 118. Microprocessor 114 controls the operation of the programmer 40 and is responsive to physician entered commands via keyboard 116, for controlling programming signals sent to the IPG 26 and operation of the video display 112 and printer 118. Also illustrated in FIG. 2 is an ECG interface 104 coupled to three ECG electrodes 106 which are intended to be placed upon the patient's body. ECG interface 104 provides sensed electrograms to input/output device 108, where they in turn may be provided to the video display 112, the central processing unit 114 or the printer 118.

FIG. 3 is a more detailed functional block diagram of the pacemaker illustrated in FIGS. 1 and 2, as connected to a human heart 10. The combined IPG circuit 300 illustrated is all located within the conductive housing 18 of the IPG 26 as illustrated in FIG. 1. The bipolar leads 14 and 16 are illustrated schematically as coupled directly to the input/output circuit 320. However, in the actual implantable device they would, of course, be coupled by means of removable electrical connectors inserted in the connector block 12 illustrated in FIG. 1.

The IPG circuit 300 is divided generally into a microcomputer circuit 302 and a pacing circuit 320. An output amplifier circuit 340 includes a ventricular pulse generator circuit coupled to the ventricle of the heart 10 by means of electrodes 30 and 28 on lead 14 as well as an atrial pulse generator circuit coupled to the atrium of heart 10 by means of atrial electrodes 20 and 22, located on lead 16. Similarly, sense amplifier circuit 360 includes atrial and ventricular sense amplifiers coupled to the atrium and ventricle, respectively, by means of leads 14 and 16. The output circuit 340 and sense amplifier circuit 360 may contain pulse generators and sense amplifiers corresponding to any of those presently employed in commercially marketed cardiac pacemakers. For purposes of explaining the present invention, it will be assumed that the atrial electrodes 20, 22 and the ventricular electrodes 28, 30 are coupled to the atrial and ventricular sense amplifiers and pulse generators, respectively, for pacing and sensing in the bipolar mode.

Sensed atrial depolarizations or P-waves that are confirmed by the atrial sense amplifier (A-event) in response to an A-sense are communicated to the digital controller/timer circuit 330 on A-event line 352. Similarly, ventricular depolarizations or R-waves that are confirmed by the ventricular sense amplifier (V-event) in response to a V-sense are communicated to the digital controller/timer circuit 330 on V-event line 354. In order to trigger generation of a ventricular pacing or V-pace pulse, digital controller/timer circuit 330 generates a trigger signal on V-trig line 342. Similarly, in order to trigger an atrial pacing or A-pace pulse, digital controller/timer circuit 330 generates a trigger pulse on A-trig line 344.

Control of timing and other functions within the pacing circuit 320 is provided by digital controller/timer circuit 330, which includes a set of timers and associated logic. Digital controller/timer circuit 330 defines the basic pacing or escape interval, which may take the form of an A—A escape interval initiated on atrial sensing (A-event) or pacing (A-pace) and triggering atrial pacing (A-pace) at the expiration thereof or may take the form of a V—V escape interval, initiated on ventricular sensing (V-event) or pacing (V-pace) and triggering ventricular pulse pacing (V-pace) at the expiration thereof. Digital controller/timer circuit 330 similarly defines the A-V delay intervals SAV and PAV that commence following a sensed A-event and a delivered A-pace, respectively. The specific values of the intervals defined are controlled by the microcomputer circuit 302 by means of data and control bus 306 from programmed in parameter values and operating modes.

Digital controller/timer circuit 330 also defines time intervals for controlling operation of the atrial and ventricular sense amplifiers in sense amplifier circuit 360. Typically, digital controller/timer circuit 330 defines an atrial blanking interval following delivery of an A-pace pulse, during which atrial sensing is disabled, as well as ventricular blanking intervals following atrial and ventricular pacing pulse delivery, during which ventricular sensing is disabled. Digital controller/timer circuit 330 also defines an atrial refractory period (ARP) during which atrial sensing is disabled or the A-event is ignored for the purpose of resetting the escape interval. The ARP extends from the beginning of the SAV or PAV interval following either an A-event or an A-trig and until a predetermined time following sensing of a ventricular depolarization or triggering the delivery of a V-pace pulse. Digital controller/timer circuit 330 similarly defines a ventricular refractory period (VRP), which is typically shorter than the portion of the ARP following ventricular sensing or pacing, following either a V-event or V-trig. In the case of an ectopic V-event, both a VRP and a post-ventricular atrial refractory period (PVARP) defined by the digital controller/timer circuit 330 separately from the ARP may be generated. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

In the embodiment illustrated in FIG. 3, the IPG 26 is provided with a piezo electric sensor 316 which is intended to monitor patient activity, in order to allow provision of DDDR rate responsive pacing, such that the defined pacing rate (A—A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 322 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. As stated above, the present invention may also be practiced in non-rate responsive pacemakers.

Data transmission to and from the external programmer 40 illustrated in FIG. 2 is accomplished by means of the telemetry antenna 334 and an associated RF transmitter and receiver 332, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited Markowitz patent.

In addition, in the context of the present invention, stimulation threshold data from a series of auto-capture test stimulation pace events may be stored in the RAM 310 or the RAM/ROM unit 314 of microcomputer 302 for later telemetry out on command of the programmer 40. This data may be encoded in digital form and transmitted via RF transmitter 332 and antenna 334 to the external programmer 40 for display and/or analysis in the form of atrial and ventricular strength-duration curves described below with reference to FIG. 5.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Microcomputer 302 controls the operational functions of digital controller/timer 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, A-event and V-event signals.

As described above, if the IPG is programmed to a rate responsive mode, the patient's activity level is monitored periodically and the escape interval is adjusted proportionally. A timed interrupt, e.g., every two seconds, may be provided in order to allow the microprocessor 304 to analyze the output of the activity circuit 322 and update the basic escape interval (A—A or V—V) of the IPG. The microprocessor 304 may also define variable A-V intervals and variable ARPs and VRPs which vary with the escape interval established in response to patient activity. For example, the microprocessor 304 may specify a variable rate adaptive decrement interval (RAD) to be subtracted from the defined A-V delay intervals when the heart rate (paced or sensed) is above a defined resting or "start" rate. Similarly microprocessor 304 may define ARPs and/or VRPs which decrease in duration in relation to an increase in sensed or paced heart rate above the start rate.

The illustrated IPG block diagram of FIG. 3 is merely exemplary, and corresponds to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a pacemaker having an architecture as illustrated in FIG. 3, and a circuit architecture as illustrated in FIG. 3 is not believed to be a prerequisite to enjoying the benefits of the present invention.

FIG. 4 is a functional flow chart of the normal operation of the pacemaker illustrated in FIGS. 1, 2 and 3 in DDD pacing mode. For the sake of simplicity, functional steps corresponding to the provision of refractory and blanking periods have been omitted, to allow for easier understanding of the overall operational mode. In the flow chart of FIG. 4, it is assumed that the basic timing of the device is based around of the definition of an atrial escape interval (A—A interval) which may be fixed or may vary as a result of the output of the physiologic sensor, e.g. the activity sensor 316 of FIG. 3 in a manner described above. This A—A interval is reset at block 400, along with the current A-V delay intervals SAV and PAV. During the A-V delay interval the device awaits either time out of the current A-V delay interval (PAV or SAV) at block 402 or ventricular sensing at block 406. If ventricular sensing (V-event) does not occur prior to A-V delay interval time out, a ventricular pacing pulse is generated at block 404 at the end of the A-V interval, and the values of the A-V intervals are updated, if necessary, at block 410.

If a ventricular depolarization or V-event is sensed at block 406, prior to expiration of the current A-V delay interval, the pacemaker's timing may optionally be reset at block 408 to deliver an atrial pacing pulse at a V-A escape interval (thereafter equal to the A—A escape interval minus the current A-V delay interval), or the device may proceed directly to updating the A-V delay intervals at block 410, and not alter the timing of the next scheduled atrial pacing pulse at the expiration of the A—A escape interval.

Following update of the base A-V delay interval at block 410, the device awaits expiration of the A—A (or optionally the V-A) escape interval at block 416, sensing of a ventricular depolarization at block 420 outside of the VRP, or sensing of an A-event at block 422, outside of the ARP. If the A—A (or V-A) escape interval expires at block 416 without any intervening A-event or V-event sensing, an A-pace pulse is generated at block 414, and the next succeeding A-V delay interval is defined to be equal to PAV at block 412, followed by reset of the A—A escape interval and the A-V delay interval at block 400.

In the event that a V-event is sensed at block 420 prior to expiration of the A—A escape interval, the timing is reset 418 to trigger A-pace at the expiration of the V-A interval (A—A escape interval minus PAV). A V-event sensed at this point is not effective to trigger an update of the SAV and PAV intervals.

If an A-event is sensed at block 422, prior to expiration of the A—A (or V-A) interval, the subsequent A-V interval is defined to be equal to SAV at block 424, and the A—A escape and A-V delay intervals are reset at block 400.

In the normal, everyday operation of the IPG, the A-pace and V-pace pulse energy in each case may be established initially by programming the pulse widths and amplitudes post-operatively or at a later patient examination. The programmed values are later, in the practice of the present invention, periodically adjusted automatically so that the normal values may fluctuate from the programmed values.

The other time interval values, including the A—A escape interval, the PAV delay interval, the ARP, VRP and any other time intervals defined by operating algorithms at any particular time are stored in either ROM or RAM and are fetched and used as described above. Thus, in the operations of the IPG in either the general algorithm of FIG. 4 or in the strength-duration (SD) algorithms described below, the specified time intervals may be fetched and employed in each designated step in response to the trigger or event signals designated in any of the algorithms.

PART II. CAPTURE DETECTION AND THRESHOLD MEASUREMENT.

Details of the stimulation threshold measurement and capture restoration features of the first aspect of the present invention incorporated into a dual chamber pacemaker of the type described above and of the second aspect of the invention incorporated into a single chamber pacemaker or the single chamber of a dual chamber pacemaker follow below. First the S-D characteristics taken into account in the operation of the invention are described in reference to FIG. 5.

Figure 5:
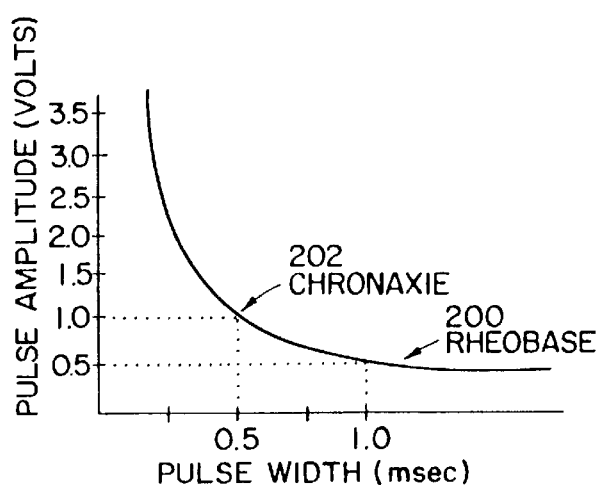
FIG. 5 is a typical strength-duration curve for cardiac stimulation signals.

FIG. 5 shows a typical S-D curve for electrical stimulation of myocardial tissue plotted as pulse amplitude in volts versus pulse width in milliseconds corresponding generally to FIG. 2 of the above-referenced '643 patent. The graph shows, inter alia, that the stimulation threshold increases with a decreasing pulse width, and thus decreases with an increasing pulse width, except that beyond the Rheobase 200, no further reductions in the amplitude threshold can be achieved. Thus, increasing the pulse width beyond about one millisecond (in the example shown) still requires a threshold of 0.5 volts. Also included on the graph for illustrative purposes is the Chronaxie 202, a measure of myocardial excitability, which is the point representing the lowest pulse width needed to have an amplitude threshold equal to twice the Rheobase threshold.

It is well known in the art to provide a safety margin between the actual delivered pacing pulse width and amplitude and the stimulation thresholds appearing in the strength-duration curve. However, as previously stated, the amount of the safety margin may change over time and must be balanced against the need to maximize battery life, as increased amplitude and pulse width will cause a greater battery energy consumption. Physiological changes in the patient may alter the thresholds from the initial programmed value or values, and can lead to loss of capture, with inadequate amplitude or pulse width.

Dual Chamber Embodiment

Figure 8A:
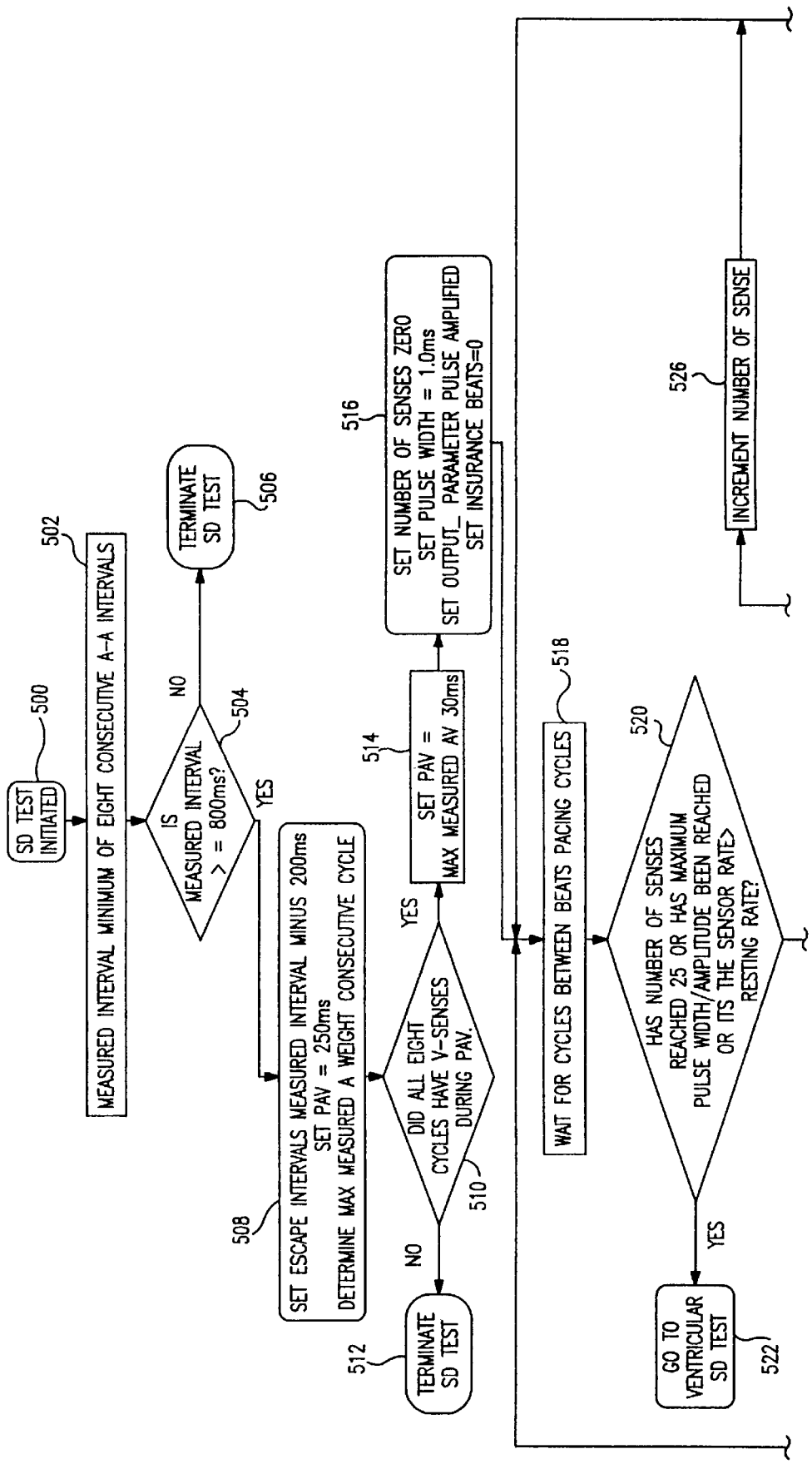
FIGS. 8 and 9 taken together depict the algorithm of one embodiment of the present invention for automatically conducting atrial and ventricular threshold tests and deriving atrial and ventricular strength-duration stimulation threshold data therefrom.
Figure 8B:
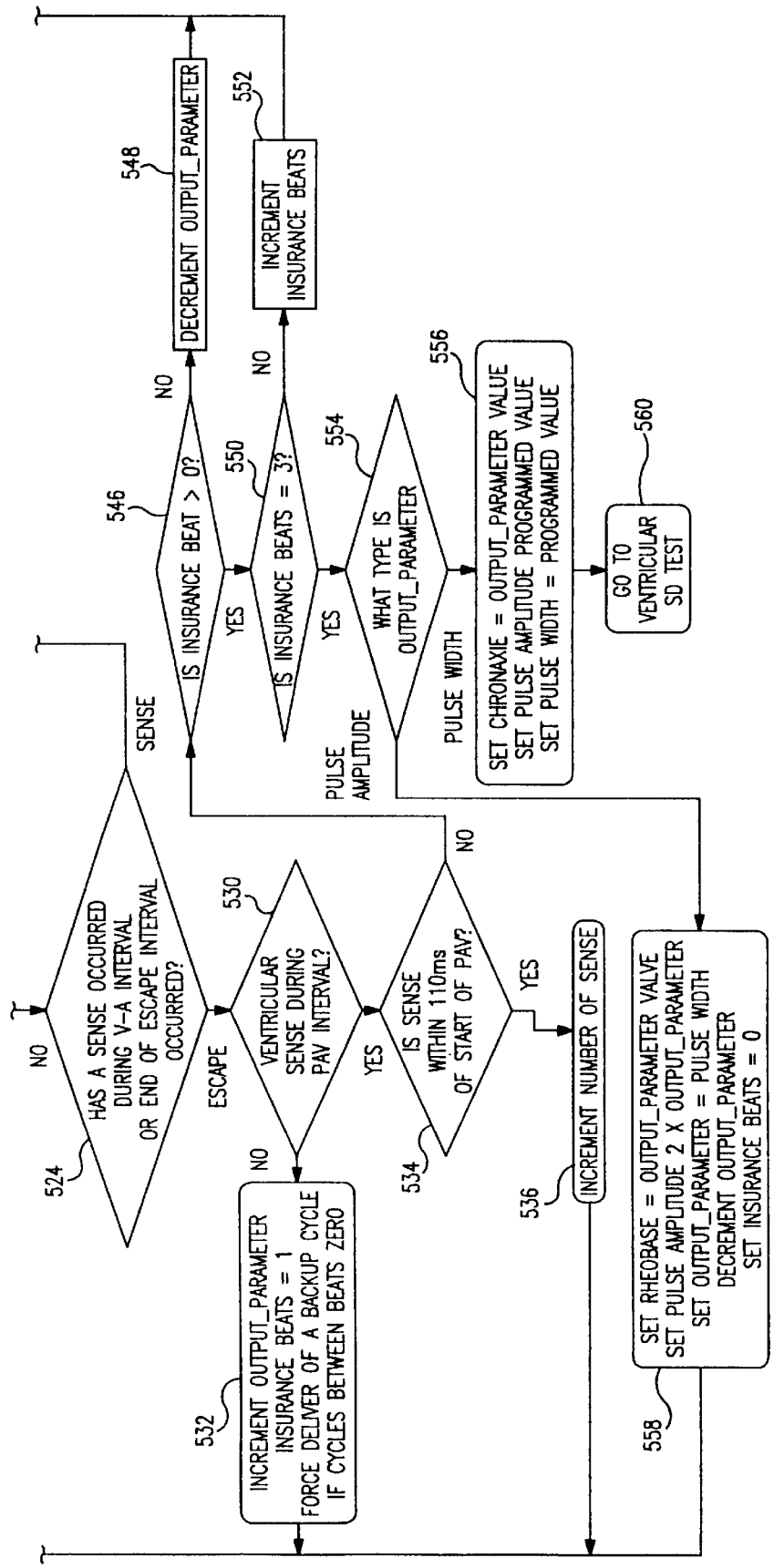
Figure 9A:
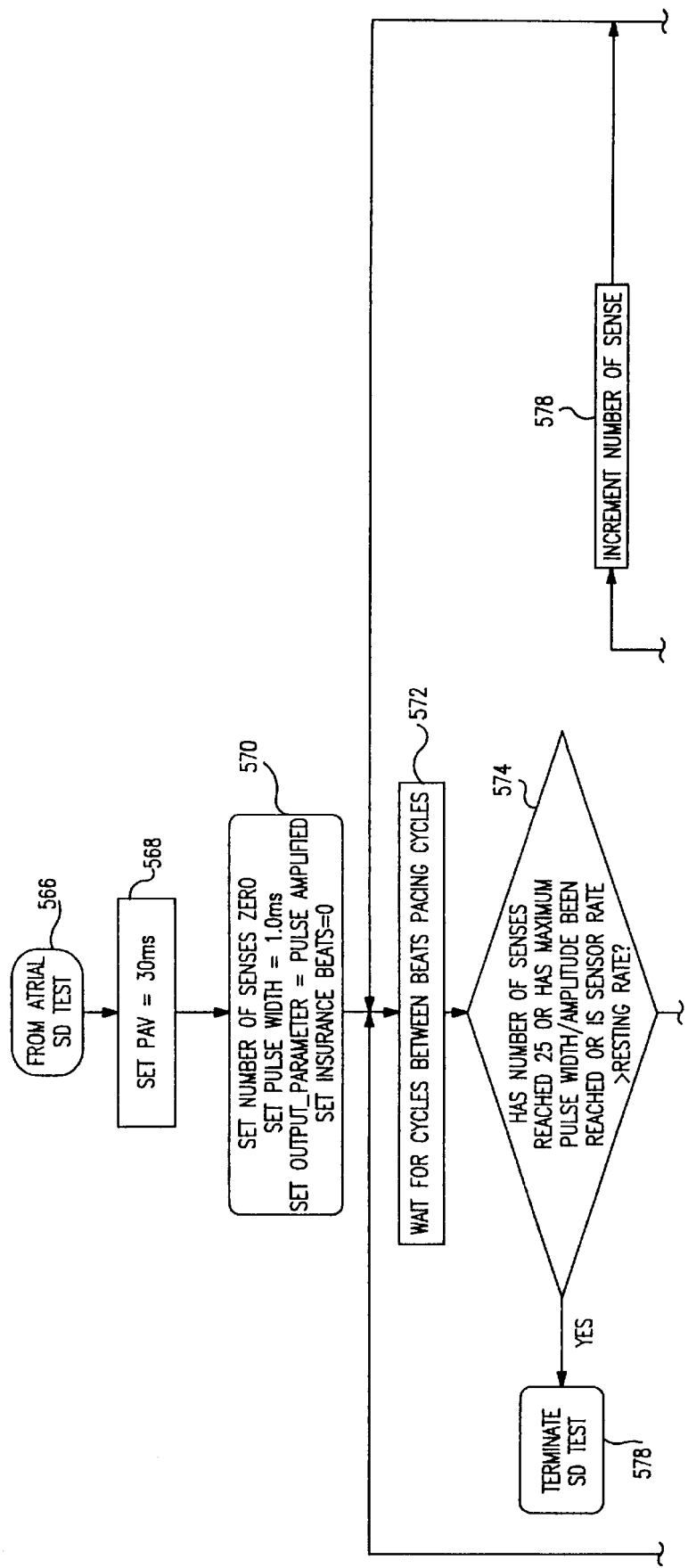
Figure 9B:
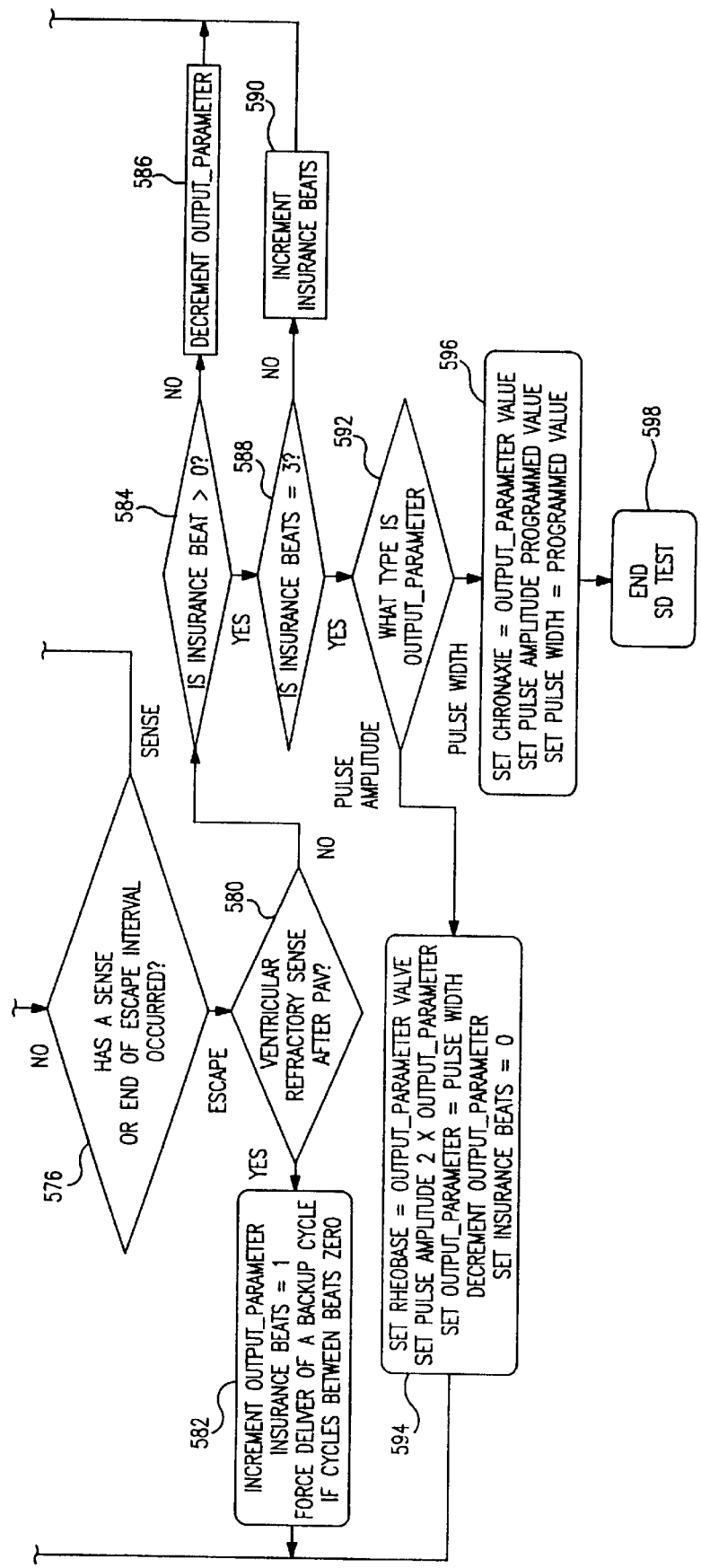

In accordance with the first aspect of the present invention, this normal pacing operation is departed from on a periodic schedule to operate under the control of the SD algorithms of FIGS. 8 and 9 for deriving both atrial and ventricular stimulation threshold data for storage in memory for telemetry out and analysis and also for use in setting the V-pace and A-pace normal pulse width and amplitude used between successive auto-capture tests in order to conserve battery energy. The pacemaker circuit 300 operating in accordance with this first aspect of the present invention is capable of detecting ALOC and VLOC in patients having a regular and predictable A-V conduction or first degree A-V block. The pacemaker circuit 300 following the ASD algorithm of FIG. 8 looks for a V-event response to a premature A-pace test stimulus during the latter portion of the PAV delay interval and declares ALOC when no V-event is detected in that interval. Following the VSD algorithm of FIG. 9, the pacemaker circuit 300 looks for a V-event in the VRP following a V-pace test stimulus delivered at the end of a test PAV interval started by an A-pace and declares VLOC when a V-event is detected in the VRP.

The microcomputer 302 may be programmed with these algorithms to periodically, e.g. every night at a certain time when the patient would be sleeping, to automatically adjust the A-pace and V-pace output amplitude and pulse width to test for atrial and ventricular stimulation thresholds. The process followed derives and stores in RAM the Rheobase and Chronaxie stimulation threshold values resulting from the tests for later telemetry out and uses the values to automatically reset the normal pacing pulse width and amplitude, reflecting a safety margin, until the next test is conducted. In the process of testing for the thresholds, capture is restored on detection of ALOC and VLOC by applied backup A-pace or V-pace pulses at programmed pulse width and amplitude energy.

The automatically adjusted parameter (amplitude or pulse width) is referred to herein as the test stimulus "test value", and the other parameter is referred to herein as the test stimulus "fixed value". The test value is adjusted throughout the stimulation threshold determination and recovery procedure described below (applicable to either ALOC or VLOC). The fixed value remains constant until the derivation of the LOC threshold values of the test value as described below.

The present invention provides a method of automatically determining atrial and ventricular pacing thresholds in patients that have normal A-V conduction or first degree A-V block. The ASD and VSD algorithm does not require any special hardware or additional circuits to detect whether an A-pace or V-pace at a test value captures the atrium or the ventricle, respectively. It simply uses the measured A-V conduction of a patient within certain time windows to determine CAPTURE or LOC. The algorithm measures at least two values for each heart chamber and records them in the IPG RAM unit 310 or RAM/ROM unit 314 of FIG. 3. The stored values may be read out by the programmer 40 of FIG. 2 and characterized as Rheobase (amplitude threshold at a pulse width of 1.0 ms) and Chronaxie (pulse width threshold at twice Rheobase) as described above with respect to FIG. 5.

The stored values for both atrial and ventricular pulse width and pulse amplitude will be the actual measured values at CAPTURE or LOC or both as determined in the course of conducting the atrial and ventricular pacing threshold tests. The actual stimulation threshold data that are stored and later characterized as Rheobase and Chronaxie may therefore be selected as either the measured value declared as LOC or CAPTURE as described below.

It is intended that the SD algorithm operate only during periods of sleep, and that, if possible, it be initiated about the same time every night by a programmed start time. The SD algorithm establishes a test pacing rate for the selected heart chamber that is clinically acceptable and not arrythmogenic but is fast enough to prevent a patient from breaking through with a sinus escape mechanism which thereby causes inhibition of the pacemaker or leads to multiple fusion events. In this regard, the pacing rate during the test should not exceed 100 bpm to avoid intolerable patient symptoms from pacing rapidly in patients who may have coronary artery disease or may be sensitive to rapid stimulation. A rate of 60 to 100 bpm is fast enough to prevent intolerable symptoms when a beat is dropped due to LOC. Ventricular rate pauses during the recovery from LOC described below should be no longer than two seconds.

The following description of the algorithms is divided into sections including the determination of ALOC and VLOC and the Atrial SD (ASD) Test and Ventricular SD (VSD) Tests. The ASD and VSD algorithms depicted in FIGS. 8 and 9 will operate only in DDI(R), DVI(R) and DDD(R) modes, i.e. with dual chamber pacing and sensing enabled with rate response to activity optionally enabled.

Atrial Loss Of Capture ALOC)

It is important to note that the algorithm that determines ALOC depends on several things including the expected characteristics of the A-V conduction consistency and delay. For example, the simplest algorithm may assume that every A-pace that results in a V-event during the A-V interval captures the atrium and every A-pace that does not result in a V-event during the A-V interval does not capture the atrium. This definition of ALOC would work if in every patient the A-V interval was very consistent in duration, if there was conduction after every A-pace that captures the atrium, and if premature ventricular contractions (PVC's) would not occur during the A-V interval. In practice, these conditions do not always prevail.

Consequently, the algorithm for determining atrial capture and ALOC is based on the assumption that A-V conduction will be quite consistent in a given patient, if the atrial pacing rate is consistent, and the following rules are followed in order.

First, if there is no ventricular sense V-event during the entire Pace A-V (PAV) interval following an A-pace test stimulus, then ALOC is declared. It is assumed that the A-pace test stimulus was below the atrial stimulation threshold.

Second, if there is a ventricular sense V-event during the PAV following a first A-pace test stimulus, then it must be determined whether the V-event resulted via the patient's A-V conduction from the capture of the atrium by the A-pace test stimulus or the V-event reflects a PVC. If the ventricular sense V-event is within the first 110 ms of the PAV, the current cycle is ignored, and ventricular safety pacing (VSP), if enabled, is allowed to pace the ventricle at the backup, programmed, V-pace values. The detection of a V-event within the 110 ms window signifies the occurrence of a PVC, because the normal, conducted, ventricular depolarization, triggered by a preceding atrial depolarization, at the maximum A-pace rate of 100 bpm employed in the threshold test regimen in humans exceeds 110 ms. If this occurs, the atrial stimulation threshold test at the same A-pace test stimulus values is repeated following the lapse of the programmed number of A—A interval Cycles Between Beats (defined below).

If the ventricular sense V-event is within the PAV and after the first 110 ms, the A-CAPTURE condition is declared or defined. Then, the A-pace test value is decremented, and the lower energy A-pace test stimulus is delivered after the requisite Cycles Between Beats.

Figure 6:
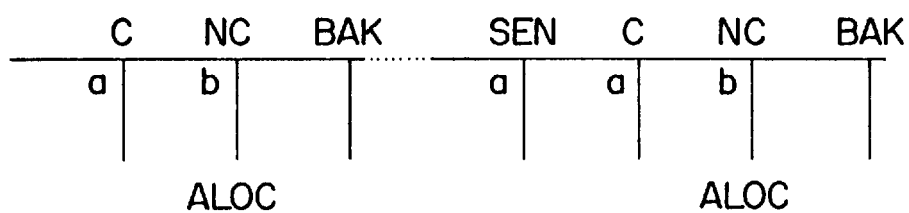
FIG. 6 is a simplified timing diagram illustrating operations of the algorithm for testing atrial stimulation threshold levels and discriminating capture from loss of capture.

FIG. 6 is a highly simplified timing diagram of a series of pacing cycles illustrating these principles with regard to the ALOC determining algorithm. The symbols 'a' and 'b' each represent the test and fixed values of each A-pace test stimulus (pulse width and amplitude test values and fixed values defined below) delivered at a test A—A interval along a time line. The symbol 'C' appearing above the time line means that a ventricular sense V-event occurred during the PAV after the immediately preceding A-pace test value indicated as the adjacent vertical line below the time line. The symbol 'NC' above the time line means that the pacemaker paced the ventricle at the end of the PAV interval with the programmed V-pace output settings. In the illustrated example, 'SEN' appearing above the time line means that a ventricular sense V-event occurred during the first 110 ms of the PAV initiated by the A-pace test stimulus of test value 'a' or was detected in the immediately preceding V-A interval. The symbol 'BAK' denotes delivery of an A-pace pulse that uses the programmed A-pace output energy settings following the NC beat. FIG. 6 thus depicts associated events illustrating the principles of ALOC and A-CAPTURE discrimination.

In FIG. 6, the first test A-pace pulse delivered at test value 'a' results in A-V conduction outside the 110 ms window. Therefore, A-CAPTURE at the test value 'a' is assumed and declared, and the test value of the next A-pace test stimulus is decreased to 'b'. For first test value 'b', the first A-pace test stimulus results in no detected V-event over the entire PAV interval. This result indicates that the A-pace test stimulus did not capture the atrium, causing the algorithm to declare ALOC, and the pacemaker to deliver the programmed V-pace at the end of the PAV interval. This pacing cycle is followed by at least one backup pacing cycle that uses the programmed atrial and ventricular pace pulse output settings at BAK.

Continuing with a further example in FIG. 6, the test value 'a' of the A-pace test stimulus is repeated after the backup pacing cycle or at another time and results in a V-event within the 110 ms window that is classified as a SEN. This beat is ignored. The next A-pace test stimuli at test value 'a' results in a V-event sensed outside the 110 ms window indicating capture and A-V conduction. Therefore, A-CAPTURE is declared, and the A-pace test value is decreased to 'b'. At the reduced energy level 'b', the first A-pace test stimulus results in no V-event detection in the PAV interval indicating a lack of atrial capture and/or A-V conduction, causing the algorithm to declare ALOC. Again, this pacing cycle is followed by at least one backup cycle that uses the programmed atrial and ventricular output settings.

In accordance with an embodiment of the present invention described below, the stimulation threshold is confirmed by next providing a series of three Insurance Beats at the previous energy level at 'a' to confirm A-CAPTURE at that energy. Alternatively, the confirmation of the threshold may be determined by repeating the delivery of the A-pace test stimulus at the energy level 'b'. Alternatively, each time an energy level results in A-CAPTURE, the same energy level may be repeated before the energy level is decreased.

Thus, ALOC is declared when it is unambiguous that the test value of the A-pace test stimulus is reduced to a point where conducted ventricular events are not present because the atrium was not captured. The setting of the A—A and PAV test intervals is set forth below in relation to the algorithms of FIGS. 8 and 9.

Ventricular Loss Of Capture (VLOC)

As with ALOC, Ventricular Loss Of Capture (VLOC) depends on several things including the expected characteristics of the A-V conduction consistency and delay. For example, the simplest VLOC and V-CAPTURE algorithm may assume: (1) that every suprathreshold V-pace delivered early in the A-V interval after an A-event or A-pace will prevent V-event detection for a period equal to the Ventricular Refractory Period (VRP); and (2) every subthreshold V-pace delivered early in the A-V interval will be followed at the expiration of the A-V interval by a conducted V-event (referred to as a "VR sense") that also falls in the VRP of that delivered test V-pace, because the failure of the subthreshold V-pace to capture does not block the A-V conduction of the preceding atrial depolarization. This definition of VLOC would work fine if PVC's did not occur during the VRP, the A-V interval was very consistent in duration, and T-Waves of the QRST complex would not be sensed, triggering a false V-event. Since these conditions are not likely, the following algorithm has been devised to determine VLOC. This VLOC (and V-CAPTURE distinguishing) algorithm is based on the assumption that PAV conduction will be quite consistent in a heart that is paced at a fixed A—A test pacing escape interval/rate.

First, if there is no ventricular sense or V-event during the VRP following a V-pace test stimulus applied at the end of the test PAV interval, then V-CAPTURE is declared. Second, if there is a V-event sensed during the VRP following such a V-pace test stimulus, then VLOC is declared. Following each declared VLOC, at least one A-pace and V-pace cycle is delivered using the programmed output settings in the next pacing cycle. Then, the V-CAPTURE threshold is confirmed by applying a series of Insurance Beats at the immediately preceding, greater V-pace test value and looking for V-CAPTURE.

Figure 7:
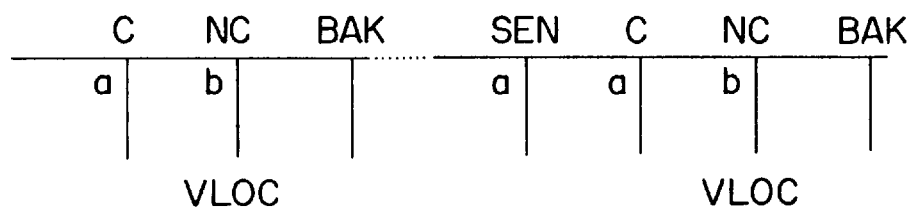
FIG. 7 is a simplified timing diagram illustrating operations of the algorithm for testing ventricular stimulation threshold levels and discriminating capture from loss of capture.

FIG. 7 illustrates the operation of the VLOC algorithm in a series of situations wherein the symbols 'a' and 'b' each represent a V-pace test value. The symbol 'C' means no V-event is detected in the VRP after the V-pace test stimulus (no VR sense) indicated below the line. The symbol 'NC' means that a V-event is detected in the VRP after the associated V-pace test stimulus. In these illustrations, the symbol 'SEN' means that a PVC occurred in the absence of a preceding V-pace test stimulus. The symbol 'BAK' denotes delivery of a V-pace pulse at the programmed output energy pulse width and amplitude settings.

In FIG. 7, the first V-pace at the test value 'a' delivered into a PAV is not followed by a VR sense. Therefore, V-CAPTURE is assumed and declared, and the V-pace test stimulus test value is decreased to 'b'. At test value 'b', the first V-pace test pulse is followed by a VR sense, causing the algorithm to declare VLOC. This A—A escape interval pacing cycle is followed by a backup A—A escape interval cycle that uses the programmed atrial and ventricular output settings at BAK.

Continuing with a second example in FIG. 7, the V-pace test stimulus at test value 'a' pulse is classified as a SEN, because a PVC occurred and was detected as a V-event (not shown) during the V-A interval immediately before this V-pace test stimulus. It is unlikely that the PVC occurring in the V-A interval will be detected as a V-event in the PAV interval, but the timing sequence could cause errors. Consequently, this beat is ignored. The next V-pace test stimulus at test energy 'a' is not followed by V-event in the VRP. Therefore, V-CAPTURE is assumed and declared, and the V-pace test stimulus test value is decreased to test value 'b'. At test value 'b', the first V-pace test stimulus is followed by a V-event during VRP, causing the algorithm to declare VLOC. Again a backup pace cycle follows.

The above described ALOC and VLOC algorithms are embodied in the ASD and VSD algorithms of FIGS. 8 and 9 which are intended to be read together in the following descriptions of the ASD Test and the VSD Test. The ASD and VSD Test algorithms are intended to derive S-D curve threshold data based on ALOC and VLOC at both amplitude and pulse width test values for storage in the microcomputer RAM for later telemetry out on command and for automatically adjusting the stimulation thresholds upward and downward for the period between successive invocation of the ASD and VSD algorithm. A number of the sets of ASD and VSD data values may be stored in RAM to telemeter out to show threshold trends over time.

In the ASD Test, as well as the VSD Test described below, the underlying time out of the specified intervals and the delivery of the A-pace and V-pace pulses described hereafter is governed by the operating program of the IPG generally depicted in FIG. 4 and described above. The ASD and VSD algorithms of FIGS. 8 and 9 provide the operating time intervals and test and fixed pace pulse and stimulus values to the general operating program and monitors events derived from the operation of the IPG as described above.

Atrial Strength-Duration (ASD) Test

The combined ASD and VSD algorithm is preferably invoked as described above during a patient's sleep, when the heart is normally at its rest rate and activity induced rate variation is minimal. Immediately after being triggered, e.g. by a built-in clock providing the time of day, the ASD Test commences at block 500 in FIG. 8 and measures eight, consecutive, intrinsic A—A intervals in block 502 to determine what A—A pacing escape interval, called the Test Rate Interval, to use during the ASD and VSD Test. Atrial refractory senses are ignored during this measurement. The intrinsic intervals measured exclude atrial refractory sense events.

The minimum of these eight consecutive A—A intervals is called the Measured Interval. At blocks 504 and 506, the ASD Test will be terminated if the Measured Interval is less than 800 ms (heart rate is measured to be above 75 bpm) to aid in accurate measurement of pacing thresholds by reducing the chance of timing conflicts between the pacemaker and the intrinsic atrial rate. In block 508, the Test Rate A—A Escape Interval for the ASD Test is set equal to the Measured Interval minus 200 ms, and the initial PAV is set at 250 ms. In DDD and DDDR modes, Non-Competitive Atrial Pacing (NCAP) is enabled and Post Ventricular Atrial Refractory Period (PVARP) is forced to 400 ms during the ASD Test. In DDI and DDIR modes, PVARP is forced to 400 ms during the ASD Test.

After the Test Rate A—A Escape Interval is set, eight beats are delivered using the initial PAV interval of 250 ms to allow for measurement of the intrinsic A-V conduction time interval in block 508. During these eight beats, all A-V intervals must end in a V-event as determined in block 510. If this doesn't happen, the ASD Test is terminated in block 512, and the Escape Interval, PAV, NCAP and PVARP are returned to the programmed settings. If all PAV intervals do end in a V-event, the maximum measured A-V interval is used to set the Max PAV interval equal to the maximum measured PAV plus 30 ms in block 514.

Each ASD Test will begin with an A-pace test stimulus set to the current programmed or operating pulse output amplitude and a 1.0 ms pulse width as set in block 516. A-pace test stimuli will be delivered once every Cycles Between Beats, where the Cycles Between Beats is an adjustable value (range 0–7). Cycles Between Beats thus represents the number of pacing cycles of A-pace and P-pace stimuli to be delivered at the initial programmed or operating pulse amplitude and width values between test cycles that contain A-pace test stimuli. It should be noted that the illustrations of FIGS. 6 and 7 have Cycles Between Beats set at zero for simplicity of illustration.

The test value parameter being changed initially during the ASD Test is pulse amplitude which will decrease as A-pace test stimuli are delivered until a test value results in the declaration of ALOC. The next set of three A-pace test stimuli uses the amplitude value from the immediately preceding set of A-pace test values that previously resulted in the declaration of A-CAPTURE. These three test stimuli are called Insurance Beats and they may be separated by the programmed Cycles Between Beats. In block 516, an Insurance Beat counter is initially set to zero. The Insurance Beats are employed and counted in steps 546–552 described below.

The Number of Senses refers to the count of Sensed events that occur inappropriately during the SD test regimen. If an A-event or a V-event (PAC, PVC, refractory ventricular sense or ventricular sense after an atrial refractory sense) occurs during the V-A interval before an A-pace test stimulus or if a V-event occurs during the first 110 ms of the PAV interval, then the A-pace test stimulus is aborted for the current test cycle and continued on the next test cycle with the same test value. This restriction includes A-event senses during PVARP. If, during the course of the ASD test, more than 25 cycles contain Senses as described above, the ASD Test will abort. At block 516, the Number of Senses counter is also initialized by setting the Number of Senses to zero. It is expected that a maximum number of aberrant A-event and V-event senses to be allowed would be on the order of 25 to allow for an infrequent PAC or PVC while avoiding pacing at the increased fixed rate in the presence of over sensing or a relatively constant tachyarrythmia.

After all counts and the starting test value is established in block 516, the ASD algorithm continues to await the completion of the programmed Cycles Between Beats in block 518. When the A-pace test cycle occurs, the A-pace test stimuli is generated, starting the A—A test cycle period, and the steps of blocks 518–560 of FIG. 8 are initiated. At decision block 520, the Number of Senses count is checked, as is the current state of the test value and the activity counter. An ongoing calculation of the activity level of the patient is conducted in parallel in the rate determination algorithm in response to the signal on line 324 of FIG. 3. If the sensor derived escape interval/pacing rate is greater than a resting rate (defined as a programmed or calculated value between the lower rate and the upper rate), then the patient is considered to be active, the ASD test is terminated, and the VSD Test algorithm is initiated in block 522. Similarly, if the Number of Senses equals 25 or if the maximum pulse width or amplitude is reached in the respective threshold tests of each energy variable, then the VSD Test algorithm is commenced in block 522. As indicated below, if these conditions persist, then the VSD Test algorithm will also be terminated.

Assuming that the ASD Test continues, a further invalid V-event may occur if a PVC V-event is sensed in the V-A interval. If this is the case, as determined in block 524, then each such instance is also counted in Increment Number of Senses block 526. If the A—A test escape interval times out instead, the A-pace test stimulus is generated and the algorithm moves to block 530 to examine the response during the PAV interval.

At block 530, the occurrence of a V-event due to a ventricular depolarization during the PAV interval is looked for. If the V-event does not occur during the PAV interval, then ALOC is assumed and declared in block 532. In block 532, the test value is incremented so that the Insurance Beats may be delivered at the incremented value, and the backup A-pace pulse at the programmed pulse width and amplitude is forced to be delivered at the next pacing cycle, if the Cycles Between Beats is set to zero. When Cycles Between Beats is programmed other than zero, the next A-pace pulse would be at the programmed or the previously determined pulse energy in any case.

If there is a V-event sensed, then it is determined in block 534 whether or not it fell within the 110 ms window from the start of the PAV interval. If it did, then the Number of Sense count is again incremented in block 536. If not, then it is presumed that A-CAPTURE has occurred, and in it is determined whether the capture was the result of one of the Insurance Beats previously generated due to an earlier ALOC in block 546. The Insurance Beats count is examined in block 546, and if it is not greater than zero, then the test value is decremented, and the wait for Cycles Between Beats is commenced in block 518.

If the count of Insurance Beats is greater than zero (as set on ALOC in block 532) but less than three, as determined in block 550, then the Insurance Beats are being delivered. On each delivery, the count of the number of Insurance Beats is incremented in block 552. Again, the wait for Cycles Between Beats is commenced in block 518 between the delivery of each Insurance Beat.

If ALOC is again encountered during the delivery of any of the Insurance Beats, then in block 532, the test value is again incremented, and the delivery of the three Insurance Beats at the new test value is repeated.

After three Insurance Beats are delivered at the same test value and A-CAPTURE is declared for all of them, as determined in block 550, then the test value output parameter being varied as the current test value is examined in block 554. If it is still the pulse amplitude, then in block 558 a number of conditions are set to record the pulse amplitude test value at ALOC, switch the test value to pulse width and the fixed value to pulse amplitude, and repeat the testing as width is reduced to ALOC. As depicted, the Rheobase value is set at the last test value of pulse amplitude and stored in the IPG RAM. The test values for both pulse amplitude ALOC and the A-CAPTURE value of the Insurance Beats may be stored in IPG RAM, and either one may be characterized as Rheobase. The pulse amplitude initial setting for pulse width ALOC determination is then set to twice the Rheobase value. Then the algorithm loops back, and the wait for Cycles Between Beats to elapse is commenced in block 518.

Thus, after the ASD pulse amplitude test is finished and Rheobase has been found, the ASD pulse width test is started. The steps 518–554 are repeated as pulse width is decreased by one step for each set of test values. When an atrial pulse width test value results in ALOC, the next set of three atrial test stimuli Insurance Beats use the pulse width value from the last set of test values that resulted in A-CAPTURE.

If all of the Insurance Beats result in A-CAPTURE, the pulse width test value at ALOC or last A-CAPTURE is recorded as Chronaxie in block 556 and stored in IPG RAM. The atrial pulse width test values of both the Insurance Beats and at ALOC may be stored in IPG RAM. The ASD threshold test is completed, and atrial pulse amplitude and width are returned to their programmed values for the duration of the VSD test.

As noted above with respect to block 520, if the amplitude reaches maximum voltage (e.g. 6 V) during the amplitude test, or the pulse width reaches maximum width (e.g. 1.5 ms) during the pulse width test, or if the sensor rate exceeds the resting rate while the ASD test is in progress, the atrial stimulation threshold test is aborted in block 522, and zero Rheobase and Chronaxie values are recorded to indicate a search failure.

Ventricular Strength-Duration (VSD) Test

The VSD Test algorithm is similar to the Atrial SD Test and commences at block 566. The parameter being changed during the VSD Test, either pulse width or amplitude is likewise called the test value, and the fixed parameter is the fixed value. For the first part of the VSD Test, the amplitude will decrease until a test value results in the declaration of VLOC. The next set of three Insurance Beat ventricular test stimuli uses the amplitude value from the preceding set of test values that resulted in the declaration of V-CAPTURE.

If all of the Insurance Beats result in V-CAPTURE, the amplitude value is recorded as rheobase, the output amplitude is doubled and the pulse width is reduced by one step. If any of the Insurance Beats result in VLOC, the algorithm assumes that capture was lost and attempts the next greater amplitude step, repeating Insurance Beats at the new test value.

These cases are identical to those of the ASD Test, and the description in that section with respect to blocks 518–560 is largely applicable to blocks 572–598 of FIG. 9. The principle of VLOC and V-CAPTURE declaration is different in that the absence or presence of a V-event in the VRP following the delivery of the V-pace test stimuli at the end of the short PAV interval is declared to be V-CAPTURE or VLOC, respectively. The V-event during the VRP following the V-pace test stimulus is examined in block 580.

The VSD Test will be initiated following the ASD Test in blocks 566, and the PAV (and SAV in DDD[R]) is set to 30 ms during the VSD Test in block 568. Each VSD Test will begin with pulse amplitude designated as the test value, and the initial V-pace test stimulus set to the current output amplitude and a 1.0 ms pulse width in block 570. The counts of the Number of Senses and the number of Insurance Beats are also set to zero in block 570. Test stimuli will be delivered once every Cycles Between Beats, where Cycles Between Beats is again the adjustable value (range 0–7). As in the ASD Test, the Cycles Between Beats represents the number of pacing cycles to be delivered between cycles that contain test stimuli.

After block 572 is satisfied, the count of the Number of Senses is examined in block 574, and if the count is 25, then the VSD Test is terminated in block 578. If the amplitude reaches 6 V during the amplitude search or the pulse width reaches 1.5 ms during the pulse width search while the Ventricular SD test is in progress, the VSD Test is aborted, and zero rheobase and chronaxie values are recorded to indicate a search failure.

At block 576, the decision block acts on the occurrence of a PVC or PAC Sense or the end of the A—A test escape interval. If a PVC or PAC Sense occurred, then the count of the Number of Senses is incremented in block 578, the cycle containing the V-pace test stimulus is ignored, and ventricular threshold test continues on the next cycle in block 572.

If the A—A escape interval ended with delivery of an A-pace, then the algorithm waits in block 580 for the delivery of the V-pace test stimulus after the 30 ms. PAV delay interval and for the occurrence of a V-event during the VRP started at delivery of the V-pace test stimulus. If a V-event is detected in the VRP, then VLOC is declared, and the test value is incremented for the Insurance Beat value, the backup pacing cycle is forced, if necessary, and the Insurance Beats count is set to one in block 582.

If a V-event is not detected in the VRP at block 580, then V-CAPTURE is declared, and the Number of Insurance Beats is examined in block 584. If the number is zero, then the test value is decremented in block 586 and the algorithm loops back to block 572 to test at the lower amplitude V-pace test stimuli. The pace test cycles repeat through blocks 572–586 until VLOC is declared, and the Insurance Beats are delivered three times per blocks 588 and 590.

The operation of delivering the Insurance Beats, recording the Rheobase value, setting the pulse amplitude fixed value and starting the VSD test with pulse width as the test value through blocks 584–592 is the same as described above with reference to blocks 546–554. As described above, both the VLOC and Insurance Beat pulse amplitude test values may also be stored in IPG RAM and one may be recorded or used as the Rheobase value. Then the VSD Test repeats for ventricular pulse width as the test value.

When the pulse width VLOC value is arrived at and the Insurance Beats are delivered, the Insurance Beat V-CAPTURE test value is recorded as the VSD Chronaxie value in block 596. The Insurance Beat and VLOC pulse width test values may also both be stored in IPG RAM. The V-pace pulse width and amplitude values are restored to the programmed value in block 596, and the VSD Test is terminated in block 598.

Thus, as the stimulation threshold data is derived in the ASD and VSD algorithms, the ALOC and VLOC pulse width and amplitude test values as well as the A-CAPTURE and V-CAPTURE test values confirmed as Insurance Beats are stored in RAM 312 or RAM\ROM unit 314 for telemetry out on command of the external programmer 40. The data may be depicted in ASD and VSD curves on the programmer display 112 or printed out on the printer 114 in a manner well known in the art using either or both sets of CAPTURE and LOC data.

Within the IPG circuit 300, the data may be used to establish or confirm the prior V-pace and A-pace pulse width and amplitude settings. The general operating program of the IPG in FIG. 4 may also invoke a resetting of the A-pace and V-pace pulse widths and amplitudes as a function of the stored values.

Simplified Single Chamber ALOC and VLOC Determination

Figure 10A:
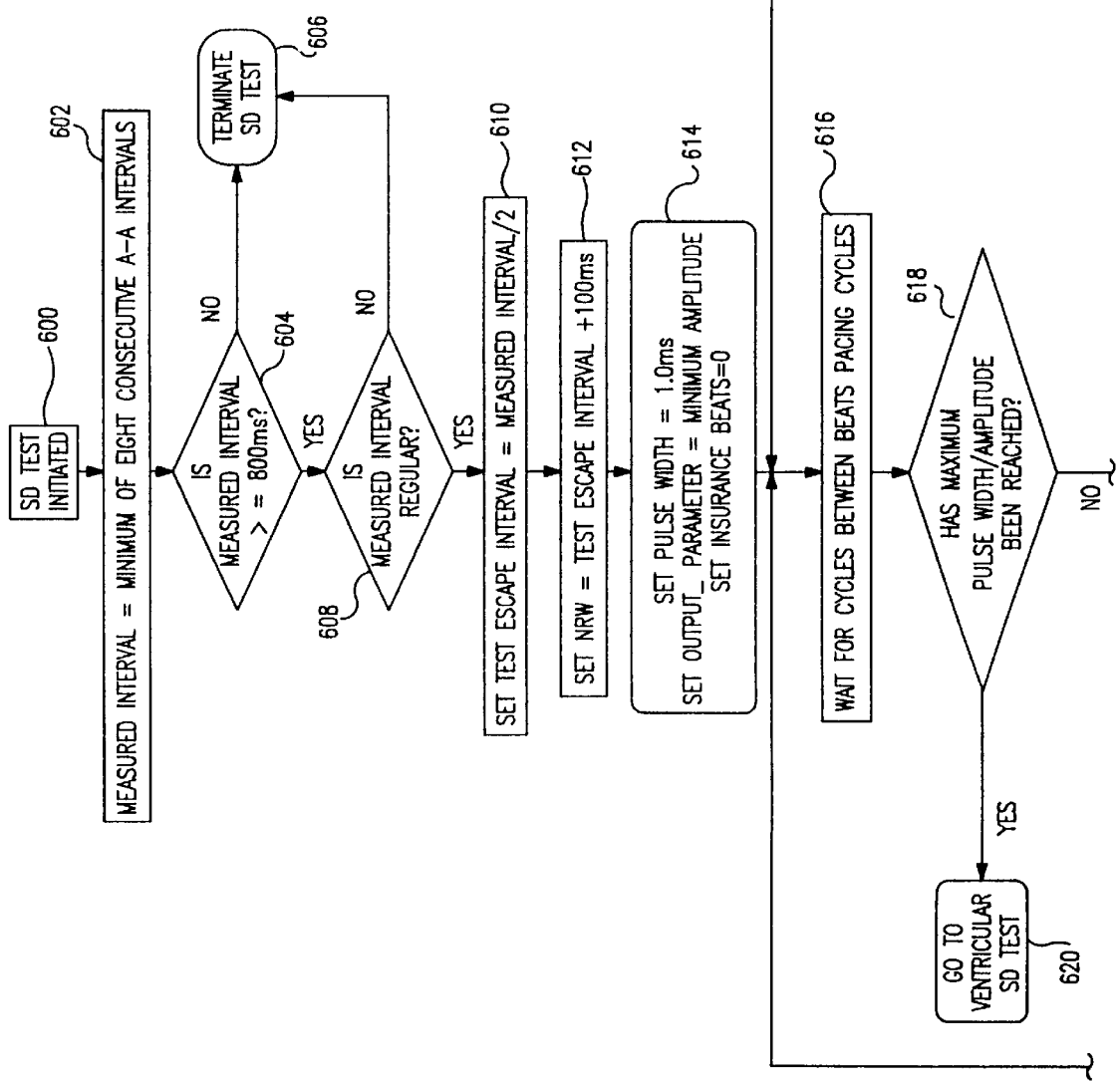
FIG. 10 depict the algorithm of a further embodiment of the present invention for automatically conducting atrial or ventricular threshold tests in the same heart chamber and deriving atrial and ventricular strength-duration stimulation threshold data therefrom.
Figure 10B:
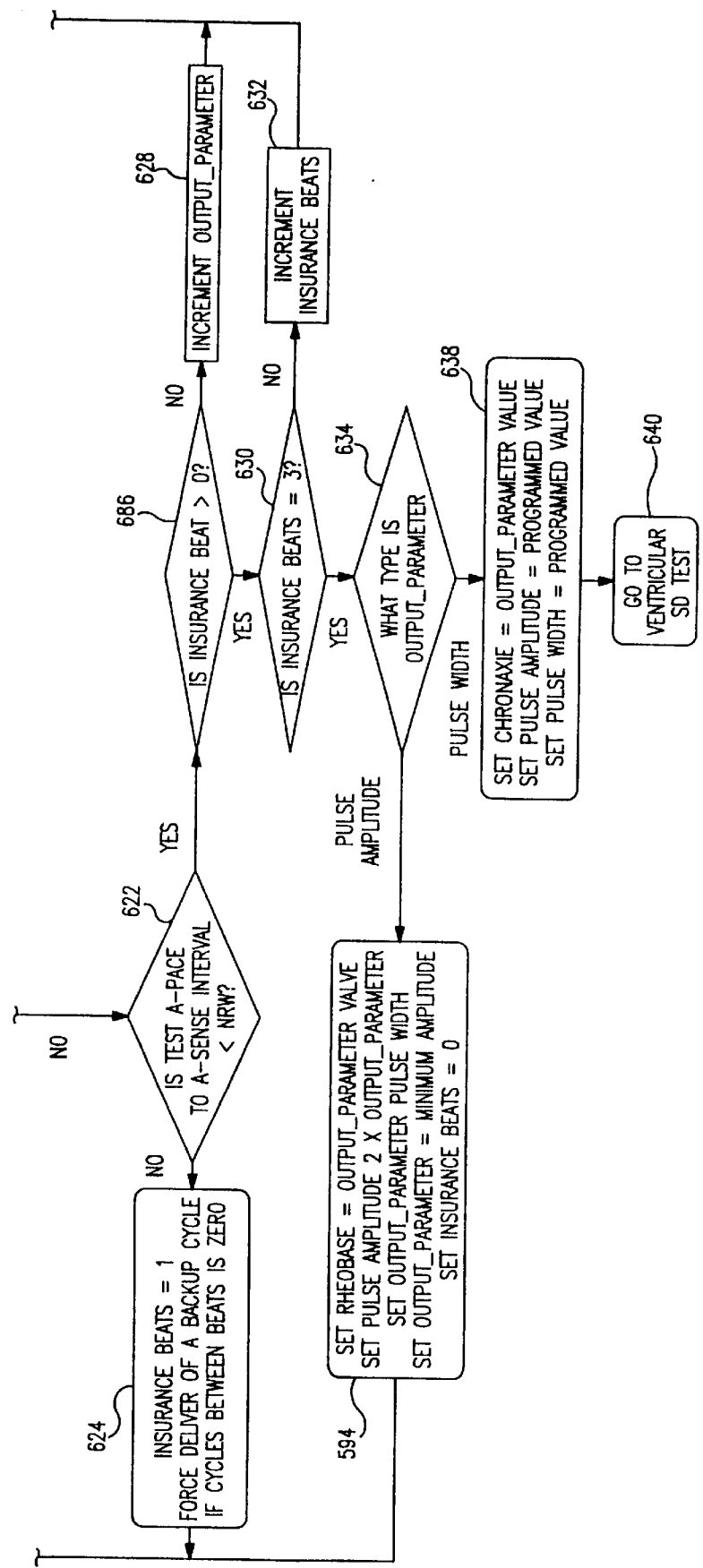

In a further embodiment of the present invention, the general inventive concept (embodied above in the VSD algorithm) of injecting a test stimulus prematurely within a pacing cycle, monitoring for a sensed event in a time window when a natural or conducted depolarization would be expected to follow a preceding natural or conducted depolarization, and declaring the absence of the sensed event as CAPTURE by the injected test stimulus and the presence of the sensed event as LOC may also be applied in a single chamber pacemaker context or operating mode for testing either atrial or ventricular stimulation thresholds or in a dual chamber pacemaker context or operating mode for sequentially testing for ALOC and VLOC and deriving ASD and VSD threshold data. The algorithm of FIG. 10 provides an alternative threshold testing mode in dual chamber IPGs implanted in patients who do not enjoy normal A-V conduction and have second or third degree block. The selection of the particular algorithm to be used in a given patient may be a programmable option in that context.

Specifically, in patient's having regular, intrinsic atrial and/or ventricular sinus rates but not necessarily having intact A-V conduction or first degree block, the alternative ASD and/or VSD algorithm as shown in FIG. 10 may be invoked periodically to test for pulse amplitude and width stimulation thresholds. In FIG. 10, the ASD test is particularized for the example of testing the atrial threshold and is initiated at block 600. The patient's intrinsic atrial sinus rate is monitored for a number of consecutive cycles in block 602. In block 604, the A—A interval lengths (or the average value thereof) are compared to the minimum interval, and the test is abandoned in block 606 if the intrinsic rate is too great, as in blocks 500–506 of FIG. 8. If the instantaneous or average rate is slow enough, then it is checked for regularity in block 608. If the measured A—A intervals are irregular beyond a certain range of regularity, then the test is also abandoned in block 606.

If the sinus rate is slow and regular enough to proceed, then the test escape interval for the test stimuli to be injected prematurely in the sinus A—A escape interval is set in block 610 to be, for example, 50% of the average measured interval. During an appropriate Not Reset Window (NRW) interval or sense test window following the delivery of the test stimulus to the heart chamber, the sense amplifier for sensing depolarizations of that same chamber is operated (after an appropriate blanking interval less than about 100 ms) to detect the following natural depolarization of the heart. The interval from the delivered test stimulus to the occurrence of the next sensed A-event is timed and the timeout is compared to the NRW. This insures that an A-event detected during the NRW will more likely than not be a natural depolarization occurring at about the average measured escape interval from the preceding A-event that signifies that the test stimulus was insufficient to capture, and ALOC is declared. If the A-event is sensed after the NRW, A-CAPTURE is assumed and declared. In block 612, NRW is set to the test escape interval (50% of the average measured A—A interval) plus 100 ms, for example.

In block 614, the test value is selected as pulse amplitude, the pulse width is set to 1.0 ms, and the Insurance Beats are set to zero. In this SD test, the Number of Senses previously employed is not considered relevant. At this point, the algorithm of FIG. 10 moves to block 616 to wait for the programmed Cycles Between Beats to count down to zero (it may be set at zero). Then in blocks 618–640 the pulse amplitude and pulse width LOC and Insurance Beat CAPTURE test values are determined in a manner analogous to that method described above with reference to blocks 572–598 of FIG. 9 with certain differences.

The first principal difference is that the test stimuli are commenced at a test pulse energy level in pulse amplitude or width that is certain to result in LOC, and the pulse amplitude or width is increased stepwise until CAPTURE is declared for the pulse width or amplitude test value. A second difference is that the Insurance Beats are set to be repeated after the delivery of a backup cycle, if necessary, at the CAPTURE threshold to verify the stimulation threshold. Since CAPTURE results in an elevated heart rate, it is desirable to avoid unnecessary repetition of the high rate pacing of the heart chamber.

In blocks 618 and 620, the ASD algorithm is abandoned at maximum pulse width or amplitude, and a VSD test may be started at block 600, if the algorithm is enabled for both chambers in a dual chamber pacemaker. At this point, the delivery of the next A-pulse at the test value and the test escape interval (i.e., the atrial test stimulus) is enabled to be delivered following the next A-event in the general operating algorithm of the IPG. At block 622, the A-sense time interval after delivery of the test stimulus is compared to the NRW, and if it is less than the NRW, ALOC is declared for that test value. In block 626, the Insurance Beat count is compared to zero, and if it is still zero (signifying that A-CAPTURE was not previously declared), then the atrial pulse amplitude test value is incremented. The next higher pulse amplitude atrial test stimulus is then delivered after satisfying blocks 616–620.

If the test stimulus energy is sufficient to capture the atrium, then the test A-pace to A-sense interval will exceed NRW in block 622, and the Insurance Beats count is incremented and a backup cycle is forced in block 624, if the Cycles Between Beats is programmed at zero. The next two A-pace test stimuli are delivered at the same pulse amplitude test value energy until block 630 is satisfied. When the delivered number is three, then, since the test value is pulse amplitude, A-CAPTURE for pulse width is declared, the Rheobase is set to the A-CAPTURE pulse width test value, and the conditions for commencing the threshold test for A-pace pulse width are all set in block 636.

IMPROVEMENT ON SINGLE CHAMBER ALGORITHM AND DEVICE FOR SINUS NODE RESET ATRIAL CAPTURE DETECTION

This improvement to the basic design provides a method for measuring atrial stimulation thresholds without dedicated capture detection hardware in either single or dual chamber pacemaker patients.

It is believed that atrial capture detection in pacemaker patients who have regular sinus rates may be obtained, as described herein. The method utilizes principles similar to those used to determine Sino-Atrial Conduction Time (SACT). SACT is defined as the time required for a sinus node depolarization to occur. Several methods have been proposed to measure SACT. The first widely accepted method was proposed by Strauss in his articles: Strauss H. C. et al., Premature Atrial Stimulation as a Key to the Understanding of Sinoatrial Conduction in Man, CIRCULATION 1973;47:86–93 and Strauss H. C. et al., Electrophysiologic Evaluation of Sinus Node Function in Patients with Sinus Node Dysfunction, CIRCULATION, 1976;53:763–776.

In this methodology described by Strauss, delivery of an atrial stimulus during the normal sinus escape interval was shown to modify sinus node rate automatically in a number of ways. The type of modification depended upon the cycle length of the premature stimulus in comparison to the sinus escape interval. The different representations of modified sinus node automatically were termed "zones." Strauss identified four zones. The sino-atrial node is depolarized in two of these zones, one of which is rare in humans and reveals bizarre and unpredictable results. Fortunately, these two zones can be differentiated easily.

When atrial premature stimuli are delivered in the correct zone (Zone II), changes in the sinus node escape interval are easily seen. Strauss used these changes to calculate the SACT. We have developed a way to use this same method in a pacemaker to determine SACT. By using this method we have found the resetting of the sinus node also indicates that the atrial stimulus is of sufficient amplitude and duration to reset the sinus node. This means that the stimulus probably captures the atrium causing a wave of depolarizing atrial tissue to reach the sinus node and depolarize it. If this is true, then atrial capture (cardiac contraction caused by a stimulus) can be assumed when a premature stimulus causes interruption of the sinus escape interval. If the sinus escape interval is not interrupted and the atrial premature stimulus was delivered at the proper time, the implication is that the stimulus must have been below capture threshold. This argument is the basis of an algorithm which we call Atrial Capture Detection via Sinus Node Reset.

The basic principles implemented in the algorithm are:

A properly timed atrial stimulus can reset a sinus escape interval.

Interruption of a stable sinus escape interval can be detected by a pacemaker.

Detection of an interrupted sinus escape interval indicates that the atrial premature stimulus depolarized the sinus node.

If the sinus node is depolarized, the entire atrium depolarized.

Using these principles in a pacemaker as is described in FIGS. 1–3 by well known digital programming techniques, those of ordinary skill can make and use this invention.

Figure 11:
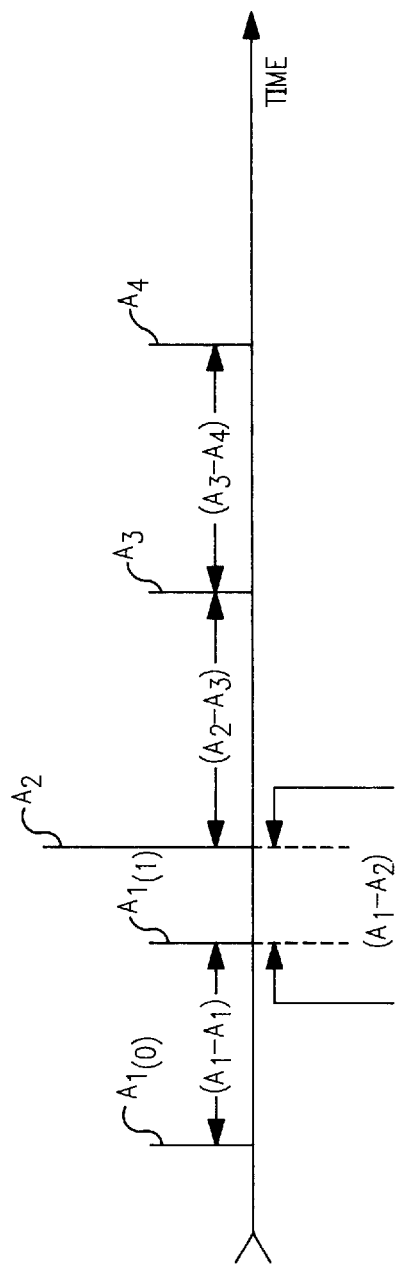
FIG. 11 is a marker channel chart of atrial senses showing depolarization time intervals.

When a measurement of SACT or a check for capture is performed, a premature atrial stimulus ($A_2$) will be generated at a test level (amplitude and/or pulse width) to follow an atrial sense at an interval ($A_1$–$A_2$) that depends on the previous sinus ($A_1$—$A_1$) cycle length (FIG. 11)

Figure 12A:
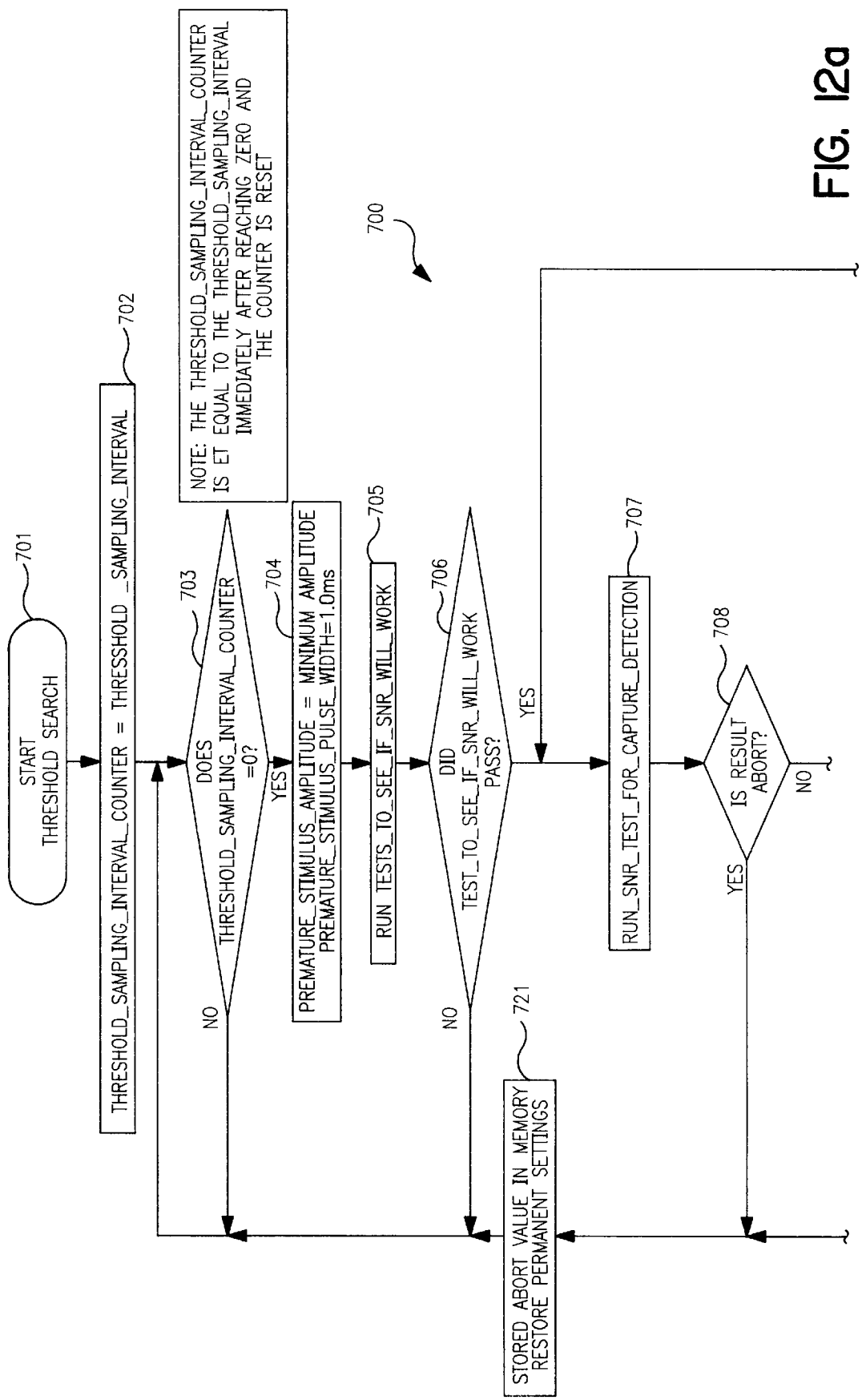
FIGS. 12, 13 and 14 are flow diagrams detailing the algorithms used for atrial capture detection via sinus node reset as implemented by the devices described herein.
Figure 12B:
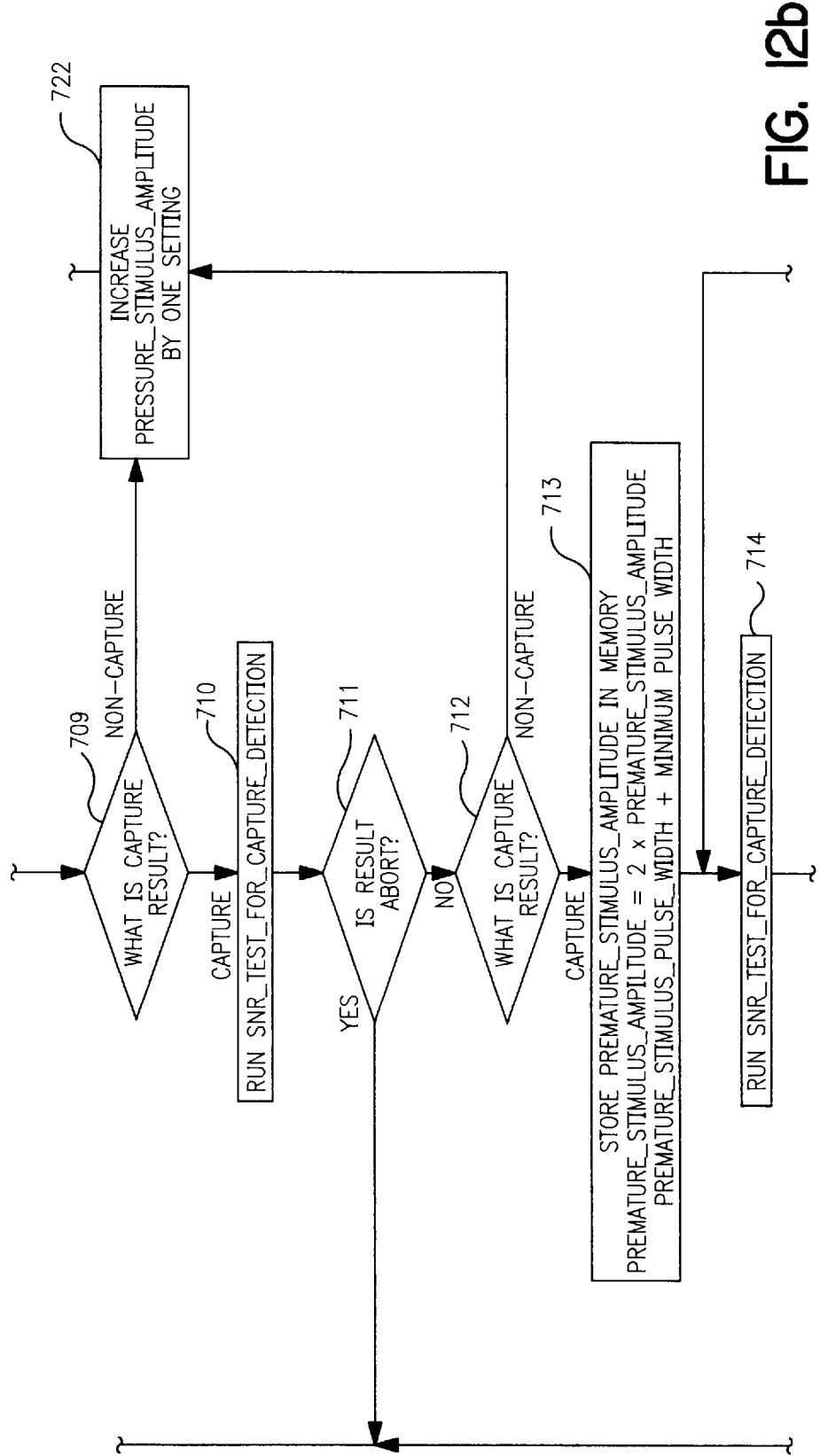
Figure 12C:
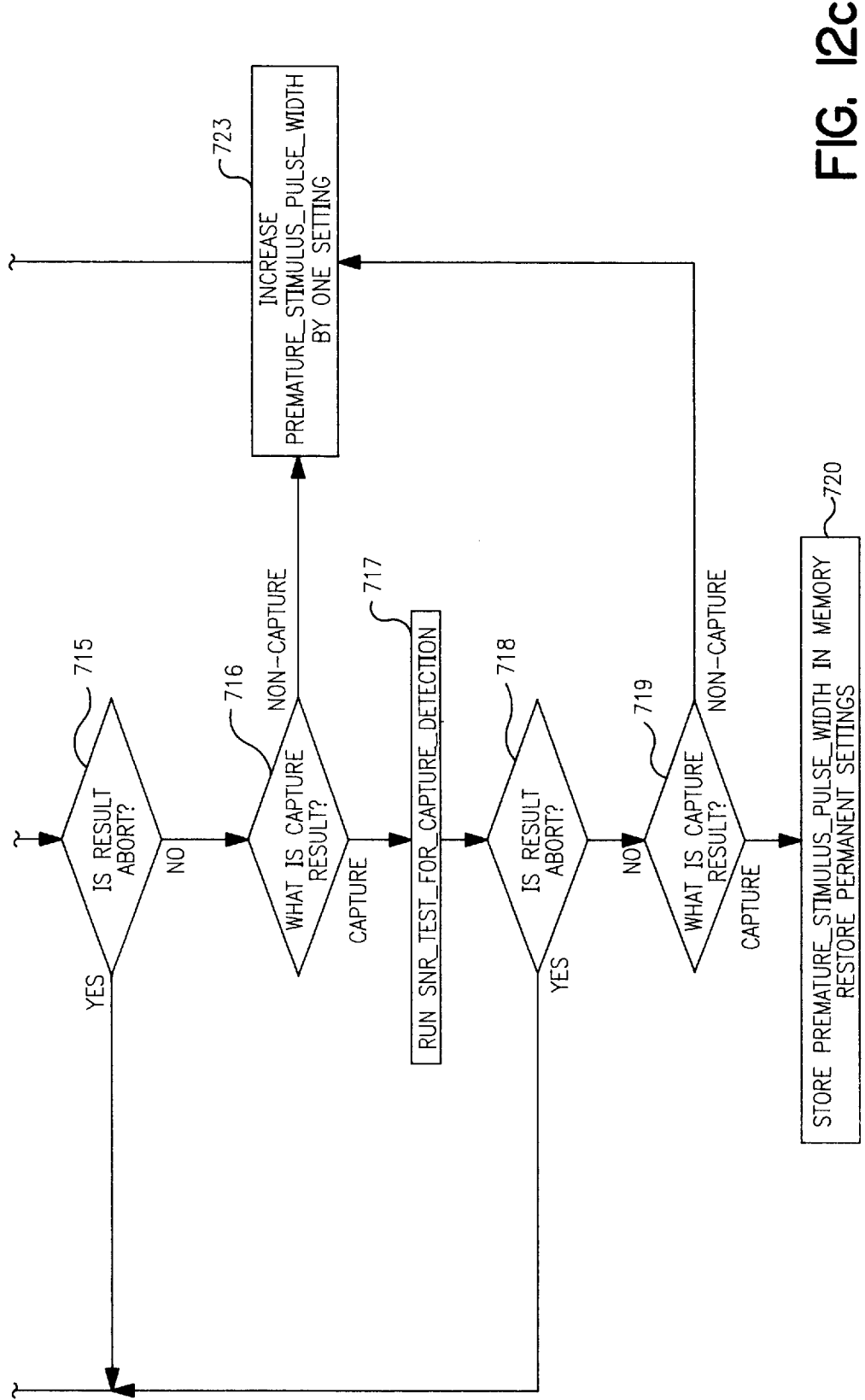
Figure 13A:
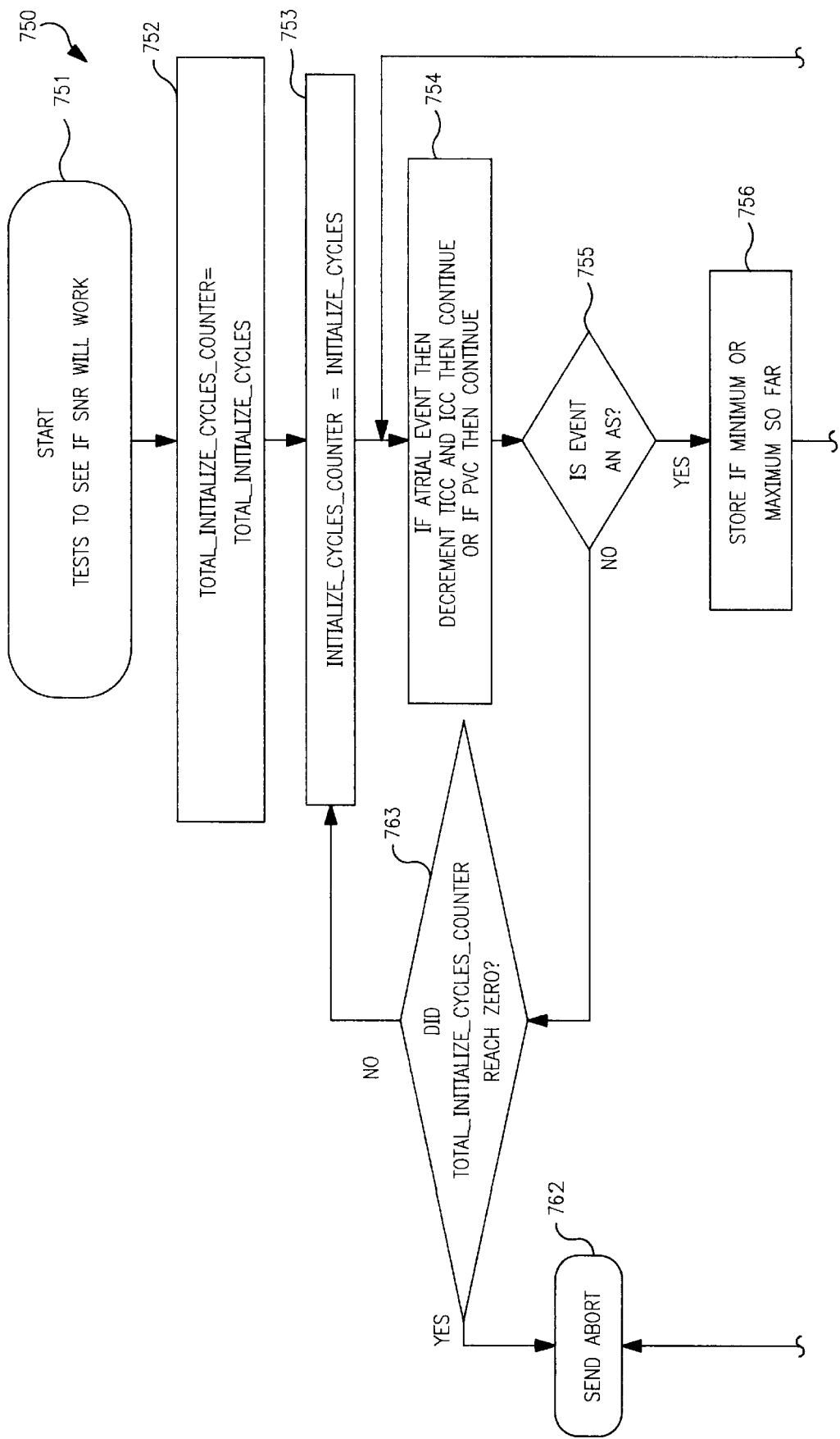
Figure 13B:
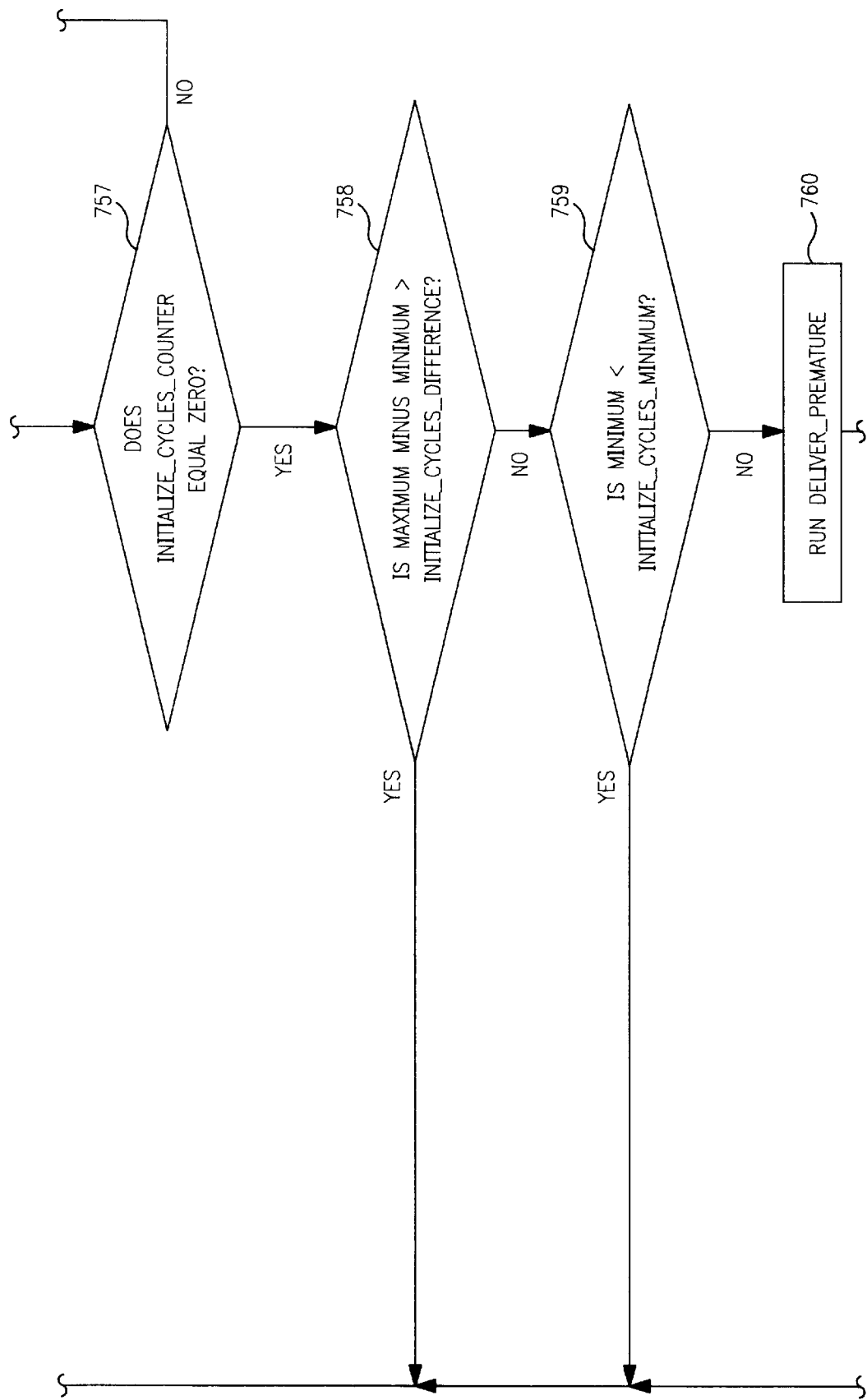
Figure 13C:
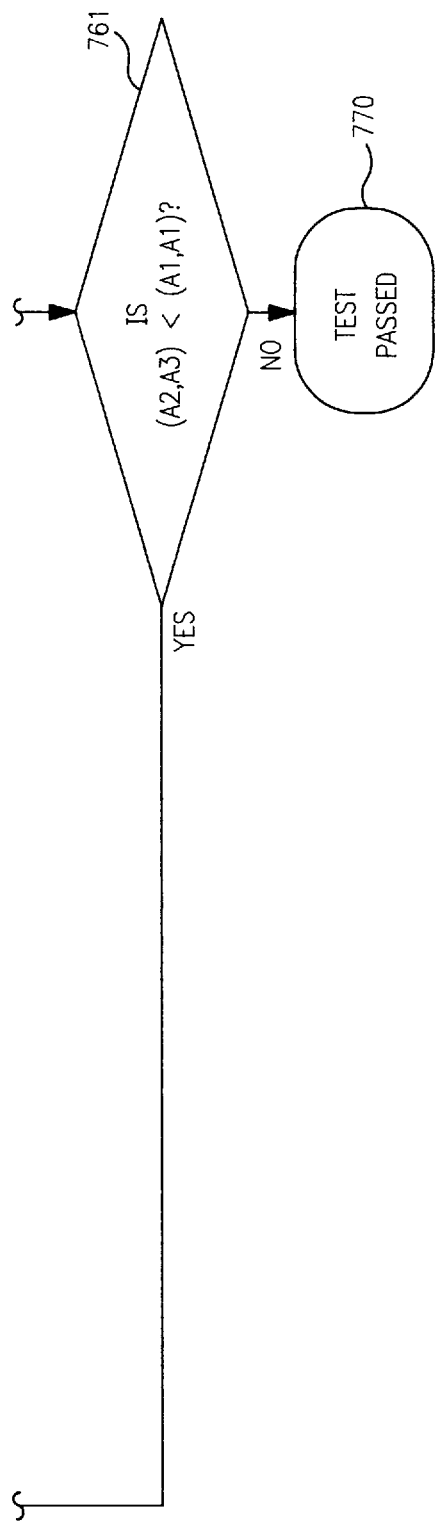
Figure 14:
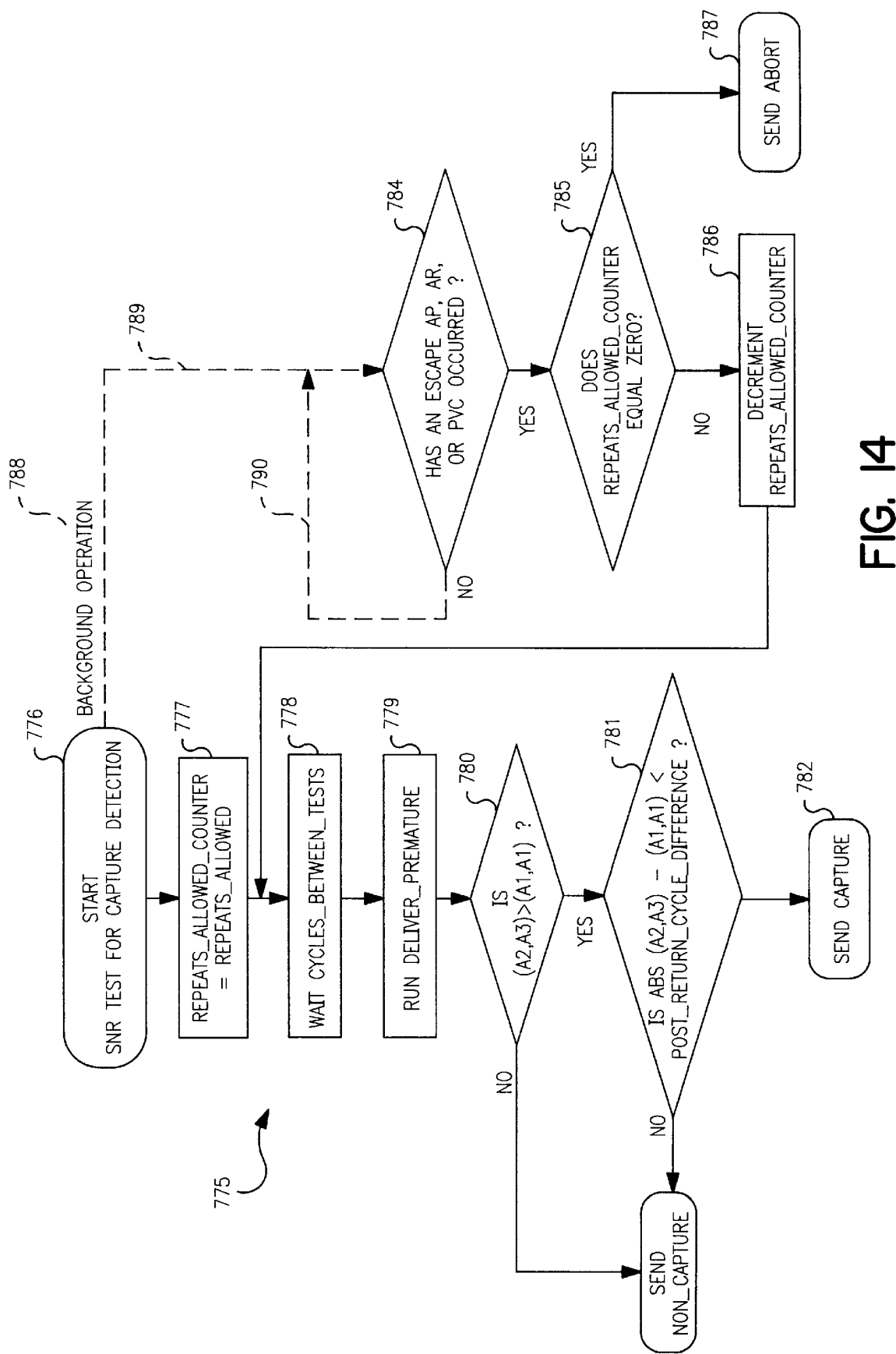

This prematurely delivered atrial stimulus will be tested using the algorithms of FIGS. 12–14 (This pulse is delivered at step 779 of FIG. 14.) ($A_1$–$A_2$) is set equal to half of ($A_1$—$A_1$) for a number of reasons. First, the study literature suggests that, a premature cycle length that is half of the sinus cycle length usually falls within Zone II, as desired to cause sinus node reset. Strauss found that many patients do not exhibit Zone II behavior when the premature stimulus is delivered at less than 40% of the sinus escape interval ($A_1$—$A_1$). Also, some patients showed Zone I behavior all the way down to 70% of ($A_1$—$A_1$). Finally, it is simple for an IPG to calculate this cycle length. We should note that the algorithm would work with other premature atrial stimulus timing interval calculation methods, as well. For example, any interval that lay anywhere between about 40% and about 70% of the cycle length would be suitable for use to time the $A_2$ pulse, but I selected half the cycle length or 50% as preferred because it is easy to implement with the current counter technology in our control circuits in our pacemaker products.

A Threshold Search is performed at a regular interval that is programmable by the user. At the beginning of each search, several checks are performed to ensure that the search will work properly. The checks made are: sinus rate measurement versus a maximum rate, sinus rate stability, excessive number of premature beats (A or V), can SACT be measured correctly.

The rate comparison is done to ensure that premature stimuli can be delivered at the appropriate times. Premature stimuli will not be delivered within 300 ms of a preceding atrial sense event. This prevents atrial competition and ensures that stimuli are delivered during a period of time when the atria can be depolarized by the stimuli.

The sinus stability check is done to make sure that the sinus rate variation is not so large that the results of a test for SACT are invalid. The idea is that stable sinus rates will provide more predictable results than sinus rates which vary significantly beat-by-beat.

If an excessive number of premature events occur in either chamber, the test for sinus node reset may have unpredictable results. This rationale is similar to that of the test for sinus rate stability.

Finally, a test for SACT must be performed to determine whether the method can be used to detect atrial capture.

Once the checks have been performed and passed, the Threshold Search may continue. By examining the interval values around each premature stimulus, (in other words, if these values indicate a sinus reset has occurred), capture or non-capture of the stimulus at a given setting is declared. The method can first check voltage or pulse width characteristics for capture efficacy in any of a number of ways as is known by those of ordinary skill. We prefer to stay with a voltage threshold search by setting the pulse width of each premature stimulus to 1.0 ms and starting at the minimum voltage. The test is repeated with the voltage increased until atrial capture is detected. In our preferred embodiment, the voltage is verified with one more capture test. If capture is observed, the voltage is stored in memory. The pulse width threshold search begins, starting at the lowest pulse width setting and a voltage that is one step above the results of the voltage threshold search. When a stimulus captures on two consecutive tests, the pulse width value is stored in memory. The Threshold Search is then declared complete.

To explain the detection of capture in detail, we first assume each premature beat is part of a test for capture. Capture is determined by comparing certain intervals after each $A_4$ occurs. First, if interval $(A_2, A_3)$ is greater than interval $(A_1, A_1)$ sinus node reset may have occurred. Strauss has shown that he takes the difference between these intervals and divided it by two to get SACT. If $(A_2, A_3)$ is less than or equal to $(A_1, A_1)$ then sinus node reset did not occur.

Strauss would next compare the $(A_3, A_4)$ interval to $(A_1, A_1)$. If they are similar, one can be certain that the sinus node was reset and that the sinus escape interval is stable. Using this information we can have a final check to ensure that the results from the premature beat are correct. It is possible that this criteria could also be removed, simplifying the algorithm, but we prefer to use this test too because it makes us surer of our result.

We initialize pacemaker parameters as follows prior to execution of this algorithm:

| Parameter | Default | Range |
|---|---|---|
| Sinus Preference (if available) | ON | |
| Threshold Sampling Interval | 2 min. | 2, 4, 10, 30, 60 min, 2, 6, 12, 24 48 hours |
| Initialize Cycles | 8 | 2–30; steps of 1 |
| Initialize Cycles counter | Initialize Cycles | |
| Total Initialize Cycles | 256 | 30–100,000; steps of 10 to 1000, then jump to 100,000 |
| Cycle Difference (CD) | 150 ms | 50, 100, 150, 200, 250, 300, 400 |
| Initialize Cycles Minimum | 600 ms | 500–1500; steps of 50 ms |
| Repeats Allowed | 5 | 0–100; steps of 1 |
| Repeats Allowed counter | Repeats Allowed | |
| Cycles Between Tests | 2 | 1–10; steps of 1 |
| Minimum Premature Interval | 300 ms | 100–1000; steps of 50 ms |

The THRESHOLD SEARCH (Step 701) of algorithmic diagram 700 is initiated each time the Threshold Sampling Interval expires. (Refer to steps 702/703 of the flow chart in FIG. 12) The Threshold Sampling Interval can be a counter or memory location holding a user programmable parameter and may be set to expire either at a given time of day or at a given interval of time. When the Threshold Sampling Interval expires it is immediately reset and restarted.

As an aside, it should be noted that the use of capitalized or partially capitalized terms in the flow diagrams 700, 750 and 755 generally mean these terms represent either a value holder(like a variable) or a program routine executable in software or some combination of software, hardware and firmware, depending on the design of the implementation, and all of which are within the ordinary skill of the reasonably skilled artisan to implement without undue experimentation based on the description herein and on the flow charts. This is a common way to explain such program sections in flow charting today. Thus where further explanation for SNR TEST FOR CAPTURE DETECTION is needed to better define the routine, I refer you to flow chart 775 from steps 707, 710, 714, and 717 of flow chart 700.

If the TESTS TO SEE IF SNR WILL WORK (Step 751 of Flow diagram 750 of FIG. 13) are passed(step 705 of flow chart 700), the actual threshold measurement can take place Otherwise the test aborts and we wait for the next sampling interval. The atrial premature stimulus amplitude is set to its minimum value and its pulse width is set to 1.0 ms(step 704). First, SNR TEST FOR CAPTURE DETECTION(step 776 and ensuing steps in diagram 775) is performed. If the result of this test is NON-CAPTURE(step 709 in diagram 700 and step 783 in diagram 775), the amplitude is increased to the next larger setting(step 722). If the result is CAPTURE (step 709 in diagram 700 and step 782 in diagram 775), a second SNR TEST FOR CAPTURE DETECTION ((710) is performed at the same output settings. If this test result is NON-CAPTURE(712), the amplitude is increased to the next larger setting(step 722). Otherwise (the result is CAPTURE), the current premature stimulus amplitude is stored in IPG memory(step 713). The output amplitude is then increased by one setting (0.5V in Thera) and the pulse width is set to its minimum value(also 713). The next SNR TEST FOR CAPTURE DETECTION(714) is performed. If the result is NON-CAPTURE(716), the pulse width is increased to the next larger setting(723). If the result is CAPTURE a second SNR TEST FOR CAPTURE DETECTION(717), is performed at the same output settings. If this test result is NON-CAPTURE, the pulse width is increased to the next larger setting(723). Otherwise (the result is CAPTURE), the current premature stimulus pulse width is stored in IPG memory(720). The output amplitude and pulse width are then reset to their programmed values.

The result of a completed Threshold Search (diagram 700)is, therefore, one stored amplitude value and one stored pulse width value. If the test is aborted(providing the inputs to step 721) during the TESTS TO SEE IF SNR WILL WORK or during SNR TEST FOR CAPTURE DETECTION a value representing an error code is stored in the memory instead.

When a THRESHOLD SEARCH is initiated, in our preferred embodiment we first make several checks to determine whether THRESHOLD SEARCH can be reliably performed. In diagram 700 this happens at step 706, for example, referring the reader to diagram 750 in which the TESTS TO SEE IF SNR WILL WORK is performed starting with step 751 of FIG. 13. The object of this diagram is to describe how Initialize Cycles of atrial sense (AS) to AS events will be detected (steps 752–757)and the minimum and maximum AS—AS intervals stored(at step 756). If an atrial event other than an AS occurs (namely an AR(Atrial Refractory, meaning it occurs in the refractory period of the pacemaker sense amp) or AP(Atrial Pace)) (found at step 755) during Initialize Cycles, the Initialize Cycles counter will be reset and Initialize Cycles will begin again on the next AS—AS interval. Ventricular events, other than pacemaker defined PVC's, are ignored. If such a PVC(Premature Ventricular Contraction) occurs, the Initialize Cycles counter is reset. Because a PVC is not an AS, the algorithm will go from 755 to 763 just like it would with an AR or AP event. Another counter called Total Initialize Cycles(found in Step 754) will continue to count each atrial cycle (defined by an atrial interval ending with an AS, AP or AR) and PVC. When the Total Initialize Cycles counter reaches Total Initialize Cycles and the Initialize Cycles Counter has been restarted, an abort condition is returned to (step 763 to step 762 to step 706 of diagram 700)THRESHOLD SEARCH.

Once Initialize Cycles completes(step 757), the minimum and maximum cycles are compared. If the maximum minus the minimum is greater than Cycles Difference(a settable parameter, of course), an abort condition is returned to THRESHOLD SEARCH (diagram 700 step 706). This criteria is intended to ensure that the search runs only if the sinus rate is stable. If the minimum is less than Initialize Cycles Minimum(another settable value) then the test is aborted until the next scheduled search. This criteria is intended to ensure that the search runs at sinus rates that are low enough to reliably detect sinus node reset. If neither of these criteria are true, one SNR TEST FOR CAPTURE DETECTION is performed. If all tests pass, the THRESHOLD SEARCH will continue.

Refer back to FIG. 11 for an example of the test for Sino-Atrial Conduction Time (SACT) proposed by Strauss, et al. Following an atrial sense $A_1$ a premature atrial pace $A_2$ is delivered at a cycle length interval $A_1,A_2$. For the purposes of this algorithm, interval $A_1,A_2$ will be set equal to half of interval $A_1,A_1$. The minimum value of interval $A_1,A_2$ is programmable, but should be nominally set to 300 ms. There is no maximum value. The pacemaker then measures interval $A_2,A_3$. The Strauss method then provides an estimation of the SACT by subtracting interval $A_1,A_1$ from interval $A_2,A_3$ and halving the result.

The result of this section of the algorithm is an array of intervals $[(A_1,A_1), (A_1,A_2), (A_2,A_3), (A_3,A_4)]$. Thus I have, here and above, described an algorithm and variations on for delivering premature atrial pulses (A2) with appropriate timing. Because interval timing variables and counters are quite different from one pacemaker to the next, it is not useful to describe in gross detail a program routine to implement this algorithm since it is clearly within the ordinary skill of the programmers of the various pacemakers. Accordingly I just call it "DELIVER PREMATURE."

The following equations are fit into the routine and calculated following each DELIVER PREMATURE(step 779 in FIG. 14, or step 760 in FIG. 13.):

Test #1(step 780 in FIG. 14, step 761 in FIG. 13.) $(A_2,A_3)$ minus $(A_1,A_1)>0$ Test #2(step 780) $[(A_1,A_2)$ plus $(A_2,A_3)]<$twice $(A_1,A_1)$ minus CD Test #3 ABS$[(A_3,A_4)$ minus $(A_1,A_1)]<$CD Where CD means Cycle Difference. The result of $(A_2,A_3)$ minus $(A_1,A_1)$ (Test #1)should be greater than zero if sinus node reset occurred. The result of $(A_1,A_2)$ plus $(A_2,A_3)$ should be less than twice $(A_1,A_1)$ (Test #2) if the stimulus actually reset the sinus node. This equation is needed to verify that sinus node reset actually did or did not occur. To ensure that slight sinus rate variations don't allow this test to pass(Test #3), a fixed amount can be subtracted from twice $(A_1,A_1)$. This means that the sum of $(A_1,A_2)$ and $(A_2,A_3)$ must less than twice $(A_1,A_1)$ by at least CD ms. The result of Test #3 should be nearly zero if capture occurred. The purpose of Test #3 is to verify that the sinus escape rate has not changed by checking to see if the AS—AS after the premature stimulus $(A_3,A_4)$ is similar to the AS—AS prior to the premature stimulus $(A_1,A_1)$. It is only used when the DELIVER PREMATURE routine is used for SNR confirmation and is not required but preferred, thus it does not appear but may be inserted into step 781 if desired. Therefore, CAPTURE is assumed if the results of some or all of these three tests are passed. Otherwise, NON-CAPTURE is assumed.

Following determination of CAPTURE or NON-CAPTURE there are Cycles Between Tests cycles (AS—AS) sensed before the $(A_1,A_1)$ sequence of the next SNR test. If any atrial refractory senses or PVC's are detected during the SNR TEST FOR CAPTURE DETECTION or if an atrial escape pace is delivered, the result of the current DELIVER PREMATURE test is ignored and DELIVER PREMATURE is repeated. DELIVER PREMATURE will be repeated Repeats Allowed times before an abort condition is produced for the THRESHOLD SEARCH.

The starting A-pace test stimulus pulse width is set to the minimum in block 636, and the steps 616–634 are repeated as the pulse width is increased until A-CAPTURE is again declared at the threshold pulse width. The Chronaxie test value is recorded, and normal A-pace pulse amplitude and width are re-confirmed in block 638. If programmed, then the VSD test is conducted in block 640. In this example, the VSD test is identical to the ASD test of blocks 600–640, with appropriate test values pre-selected. Although the SD algorithm of FIG. 10 is particularly characterized for ASD testing, it will be understood that the algorithm may be used for VSD testing alone in the same fashion, using the ventricular pulse generator and sense amplifier.

Other Applications and Embodiments of the Invention

Although the above described ASD and VSD algorithms of FIGS. 8–10 contemplate being invoked at a particular time of day when a patient is at rest, it will be understood that the principles of the invention may be invoked at other times to test for LOC. In blocks 516, 570 and 614, the Cycles Between Beats are set so that the delivery of the test stimuli may be either sequential or separated by normal pacing cycles up to a programmable maximum number. It will also be understood that the inventive stimulation and detection concepts may be employed to periodically test either ventricular or atrial capture in a shortened test escape interval by delivering a test A-pace or V-pace stimuli at a selected reduced energy so that a record of each declared A-CAPTURE/V-CAPTURE or ALOC/VLOC can be stored in IPG RAM with the associated time of day and/or other operating conditions for later telemetry out and diagnostic study. For example, such a record may be compiled correlated to the patient's activity level or current pacing rate as determined contemporaneously by the activity sensor.

The algorithms presented in FIGS. 8–10 and the above variations may also be simplified and performed with simple reductions in pace pulse energy, e.g. pulse amplitude or width or preset combinations of both, without deriving S-D threshold data in the manner described. In addition, the threshold tests following the principles of the present invention may be invoked by remote triggering employing the programmer or a simplified triggering device.

Other applications of the inventive method of delivering the test stimuli from the conventional atrial and ventricular pulse generators and detecting the responses from the conventional sense amplifiers and pace/sense electrodes in the manner described above will be apparent to those of skill in the art.

Although the present invention is described in conjunction with a microprocessor-based architecture, it will be understood that it could be implemented in other technology such as digital logic-based, custom integrated circuit (IC) architecture, if desired. It will also be understood that the present invention may be implemented in dual-chamber pacemakers, cardioverters, defibrillators and the like.

Variations and modifications to the present invention are possible given the above disclosure. However, such variations and modifications are intended to be within the scope of the invention claimed by this Letters Patent.

We claim:

1. In a pacemaker pulse generator having a pulse generator for generating and applying pacing pulses to a chamber of the heart to evoke a stimulated depolarization and capture the heart and a sense amplifier for sensing natural depolarizations of the heart, a method of testing for the stimulation threshold energy of the pacing pulses sufficient to capture the heart comprising the steps of:

determining a time interval in which a natural depolarization of the heart would be expected to follow a preceding natural or stimulated depolarization and defining a test window encompassing at least a portion of the time interval;

applying a test pacing pulse at a test energy level to the heart at a point during the determined time interval and prior to an expected natural depolarization following a preceding natural or stimulated depolarization;

operating the sense amplifier during the test window to detect a depolarization of the heart;

declaring capture of the heart by the test pacing pulse if a depolarization of the heart is not sensed in the test window; and declaring loss of capture of the heart by the test pacing pulse if a depolarization of the heart is sensed in the test window.

2. In a pacemaker pulse generator having an atrial pulse generator for generating and applying atrial pacing pulses to the atrium of the heart to evoke a stimulated depolarization and capture the atrium and a ventricular sense amplifier for sensing natural depolarizations of the ventricle, a method of testing for the stimulation threshold energy of the atrium comprising the steps of:

determining the patient's atrial escape interval;

operating said atrial pulse generator to deliver an atrial test stimulus at a test energy to the atrium in said atrial escape interval timed to capture the atrium if the test energy is sufficient to capture the atrium;

setting a paced A-V delay interval;

operating the ventricular sense amplifier during at least a portion of the paced A-V delay interval to sense a depolarization of the ventricle;

declaring capture of the atrium by the atrial test pacing pulse if a depolarization of the ventricle is sensed in the paced A-V delay interval; and declaring loss of capture of the atrium by the atrial test pacing pulse if a depolarization of the ventricle is not sensed in the paced A-V delay interval.

3. In a pacemaker pulse generator having a pulse generator for generating and applying pacing pulses to the one chamber of the heart to evoke a stimulated depolarization and capture the heart chamber and a sense amplifier for sensing natural depolarizations of the heart chamber, a method of testing for the stimulation threshold energy of the heart chamber comprising the steps of:

determining the heart chamber's sinus escape interval;

operating the pulse generator to deliver a test stimulus at a test energy to the heart chamber during said escape interval timed to capture the chamber if the test energy is sufficient to capture;

setting a sense time window;

operating the sense amplifier during the sense window to detect a depolarization of the chamber;

declaring loss of capture of the chamber by the test stimulus if a depolarization of the chamber is sensed in the sense time window; and declaring capture of the chamber by the test stimulus if a depolarization of the chamber is not sensed in the sense time window.

4. In a pacemaker pulse generator having a pulse generator for generating and applying pacing pulses to a chamber of the heart to evoke a stimulated depolarization and capture the heart and a sense amplifier for sensing natural depolarizations of the heart, apparatus for testing for the stimulation threshold energy of the pacing pulses sufficient to capture the heart comprising:

means for determining a time interval in which a natural depolarization of the heart would be expected to follow a preceding natural or stimulated depolarization and defining a test window encompassing the end of the time interval;

means for operating said pulse generator to apply a test pacing pulse at a test energy level to the heart at a point during the determined time interval and prior to an expected natural depolarization following a preceding natural or stimulated depolarization;

means for operating said sense amplifier during the test window to detect a depolarization of the heart;

means for declaring capture of the heart by the test pacing pulse if a depolarization of the heart is not sensed in the test window; and means for declaring loss of capture of the heart by the test pacing pulse if a depolarization of the heart is sensed in the test window.

5. In a pacemaker pulse generator having a pulse generator for generating and applying pacing pulses to the one chamber of the heart to evoke a stimulated depolarization and capture the heart chamber and a sense amplifier for sensing natural depolarizations of the heart chamber, apparatus for testing for the stimulation threshold energy of the heart chamber comprising:

- means for determining the heart chamber's sinus escape interval;
- means for operating the pulse generator to deliver a test stimulus at a test energy to the heart chamber during said escape interval timed to capture the chamber if the test energy is sufficient to capture;
- means for setting a test time window;
- means for operating the sense amplifier during the test window to detect a depolarization of the chamber;
- means for declaring loss of capture of the chamber by the test stimulus if a depolarization of the chamber is sensed in the test time window; and
- means for declaring capture of the chamber by the test stimulus if a depolarization of the chamber is not sensed in the test time window.

6. In a pacemaker pulse generator having a pulse generator for generating and applying pacing pulses to a chamber of the heart to evoke a stimulated depolarization and capture the heart and a sense amplifier for sensing natural depolarizations of the heart, apparatus for testing for the stimulation threshold energy of the pacing pulses sufficient to capture the heart comprising:

- means for determining a time interval in which a natural depolarization of the heart would be expected to follow a preceding natural or stimulated depolarization and defining a test window encompassing the end of the time interval;
- means for operating said pulse generator to apply a test pacing pulse at a test energy level to the heart at a point during the determined time interval and prior to an expected natural depolarization following a preceding natural or stimulated depolarization;
- means for operating said sense amplifier during the test window to detect a depolarization of the heart;
- means for declaring capture of the heart by the test pacing pulse if a depolarization of the heart is not sensed in the test window; and
- means for declaring loss of capture of the heart by the test pacing pulse if a depolarization of the heart is sensed in the test window.

7. A pacemaker adapted to execute a method as set forth in claim 1 wherein said method further comprises:

- said step of applying a test pacing pulse includes;
- activating a routine to deliver said pulse prematurely.

8. A pacemaker as set forth in claim 7 wherein activation of said routine occurs during a test for SNR capture detection routine.

9. A pacemaker as set forth in claim 7 wherein activation of said routine occurs during a test to see if SNR will work routine.

10. A pacemaker as set forth in claim 7 wherein the delivery of said applied test pulse is timed to be from about 30 to 70% of the time from a pair of sequential A1 senses.

* * * * *